United States Patent
Fujikura et al.

(10) Patent No.: US 9,803,223 B2
(45) Date of Patent: Oct. 31, 2017

(54) CORYNEFORM BACTERIUM TRANSFORMANT WITH IMPROVED ANILINE PRODUCTIVITY AND PROCESS FOR PRODUCING ANILINE USING THE SAME

(71) Applicants: RESEARCH INSTITUTE OF INNOVATIVE TECHNOLOGY FOR THE EARTH, Kyoto (JP); SUMITOMO RUBBER INDUSTRIES, LTD., Hyogo (JP)

(72) Inventors: Keitarou Fujikura, Hyogo (JP); Kazumi Hiraga, Kyoto (JP); Masayuki Inui, Kyoto (JP); Hideaki Yukawa, Kyoto (JP)

(73) Assignees: RESEARCH INSTITUTE OF INNOVATIVE TECHNOLOGY FOR THE EARTH, Kyoto (JP); SUMITOMO RUBBER INDUSTRIES, LTD., Hyogo (JP)

( * ) Notice: Subject to any disclaimer, the term of this patent is extended or adjusted under 35 U.S.C. 154(b) by 50 days.

(21) Appl. No.: 14/782,893

(22) PCT Filed: Mar. 4, 2014

(86) PCT No.: PCT/JP2014/055521
§ 371 (c)(1),
(2) Date: Oct. 7, 2015

(87) PCT Pub. No.: WO2014/171205
PCT Pub. Date: Oct. 23, 2014

(65) Prior Publication Data
US 2016/0068876 A1    Mar. 10, 2016

(30) Foreign Application Priority Data

Apr. 17, 2013    (JP) .................................. 2013-086693

(51) Int. Cl.
| | |
|---|---|
| *C12P 13/00* | (2006.01) |
| *C12N 1/21* | (2006.01) |
| *C12N 9/88* | (2006.01) |
| *C12N 1/20* | (2006.01) |

(52) U.S. Cl.
CPC .............. *C12P 13/001* (2013.01); *C12N 1/20* (2013.01); *C12N 9/88* (2013.01); *C12Y 401/01024* (2013.01)

(58) Field of Classification Search
None
See application file for complete search history.

(56) References Cited

U.S. PATENT DOCUMENTS

| 7,151,202 B1 | 12/2006 | Yamada et al. |
| 2005/0003985 A1 | 1/2005 | Kottwitz et al. |
| 2008/0242823 A1 | 10/2008 | Fujikura |
| 2013/0302860 A1 | 11/2013 | Yukawa et al. |

FOREIGN PATENT DOCUMENTS

| JP | 2001-333784 | 12/2001 |
| JP | 2005-507259 | 3/2005 |
| JP | 2008-274225 | 11/2008 |
| WO | 2012/090978 | 7/2012 |

OTHER PUBLICATIONS

Merriam-Webster online dictionary definition of "represent", last viewed on Apr. 19, 2017, 1 page.*
International Search Report dated Jun. 17, 2014 in International (PCT) Application No. PCT/JP2014/055521.
Fujikura et al., "Screening and characterization of decarboxylase for production of aniline in *Corynebacterium glutamicum*", Proceedings (online) of the Annual Meeting 2013 Sendai of Japan Society for Bioscience, Biotechnology, and Agrochemistry, Mar. 5, 2013, with English translation.
Fujii et al., "Improvement of Amylomaltase from *Thermus aquaticus* by Random and Saturation Mutageneses", J. Appl. Glycosci., vol. 52, No. 2, 2005, pp. 137-143.
Inoue, "Synthesis of Bio-Aniline: Reduction of Nitrobenzene by Immobilized Baker's Yeast", Chemical Education, vol. 39, No. 5, 1991, pp. 572-573, with partial English translation.
Sloane et al., "Studies on the Metabolism of p-Aminobenzoic Acid by *Mycobacterium smegmatis*", The Journal of Biological Chemistry, vol. 193, 1951, pp. 453-458.
McCullough et al., "Enzymatic Decarboxylation of the Aminobenzoates", Journal of the American Chemical Society, vol. 79, 1957, pp. 628-630.
Fujikura et al., "Screening and characterization of decarboxylase for production of aniline in *Corynebacterium glutamicum*", the Annual Meeting 2013 Sendai of Japan Society for Bioscience, Biotechnology, and Agrochemistry, Mar. 26, 2013, with English translation.
International Preliminary Report on Patentability and Written Opinion of the International Searching Authority dated Oct. 20, 2015 in International (PCT) Application No. PCT/JP2014/055521.

* cited by examiner

*Primary Examiner* — David Steadman
(74) *Attorney, Agent, or Firm* — Wenderoth, Lind & Ponack, L.L.P.

(57) ABSTRACT

An objective of the present invention is to provide a microorganism capable of efficiently producing aniline from aminobenzoic acid, and a process for efficiently producing aniline from aminobenzoic acid. To achieve the objective, provided is an aniline-producing transformant constructed by introducing a gene which encodes an enzyme having aminobenzoate decarboxylase activity into a coryneform bacterium as a host, characterized in that the enzyme having aminobenzoate decarboxylase activity is composed of an amino acid sequence which is the same as that represented by SEQ ID NO: 2 except for having a mutation of at least proline (P) at position 309 from the N terminus.

15 Claims, 2 Drawing Sheets

SEQUENCE LISTING

```
<160> NUMBER OF SEQ ID NOS: 44

<210> SEQ ID NO 1
<211> LENGTH: 1428
<212> TYPE: DNA
<213> ORGANISM: Enterobacter cloacae

<400> SEQUENCE: 1
atggcatttg atgatttgag aagcttcctg caggcgctag atgagcaagg gcaactgctg     60
aaaattgaag aagaggtcaa tgcggagccg gatctggcg cggccgctaa cgcgacggga    120
cgtatcggtg atggtgcgcc tgcgctgtgg ttcgataaca ttcgcgggtt taccgatgcc    180
agggtggtga tgaacaccat cggctcctgg cagaaccacg ccatttcgat ggggctgccg    240
gcgaataccc cggtcaaaaa gcagatcgat gagtttattc gccgctggga taaattcccg    300
gtcgcaccgg agcgccgggc caacccgca tgggcgcaga atacggtgga cggtgaggag    360
attaacctgt tcgacatcct gccgctgttt cgcctgaacg acggggacgg cggttttat    420 ctcgacaaag cgtgcgttgt ctcgcgcgat ccgctcgacc cggaccattt cggcaagcag    480
aacgtcggta tttaccgcat ggaagtgaag ggcaaacgta agctcggcct gcagccggtg    540
ccgatgcatg atatcgccct gcatctgcat aaagccgaag agcgtggtga agacctgccg    600
attgcgatta cgttgggcaa cgatccgatc atcaccctga tgggcgcaac gccgctgaaa    660
tacgatcagt ccgagtatga aatggccggg gcgctgcgtg aaagcccgta cccgattgcg    720
accgcgccgt tgaccggctt cgatgtgccg tggggtctg aagtgatcct ggaagggggtg    780 attgaaggcc gtaaacgtga aattgaaggg ccgttcggtg agtttaccgg gcactattcg    840
ggcggacgca atatgacggt ggtccgtatt gataaagtct cgtaccgcac caaaccgatt    900
ttcgaatccc tctatctcgg gatgccctgg accgagatcg actacctgat ggggccagcc    960
acctgtgtgc cgcttttacca gcaactgaaa gcggagttcc ctgaagtgca ggcggtgaac   1020
gcgatgtata cccacggtct gctggcgatc atctccacca aaaaacgcta cggtggttt   1080 gcccgcgcgg tcggtttacg cgccatgacc acgccgcatg gcctgggcta tgtgaagatg   1140
```

```
gtgattatgg tggatgaaga tgtcgatccg ttcaacctgc cgcaggtgat gtgggcgctg    1200
tcatcaaaag tgaacccggc aggggatctg gtgcagctgc cgaacatgtc ggttcttgag    1260
cttgatcctg ggtccagccc ggcaggcatc accgacaagc tgattattga tgccaccacg    1320
cctgttgcgc cggataaccg cggtcactac agccagccgg tgcaggattt acctgaaacc    1380
aaagcctggg ctgaaaagct gactgcgatg ctggcagcac gccaataa                1428
```

<210> SEQ ID NO 2
<211> LENGTH: 475
<212> TYPE: PRT
<213> ORGANISM: Enterobacter cloacae

<400> SEQUENCE: 2

Met Ala Phe Asp Asp Leu Arg Ser Phe Leu Gln Ala Leu Asp Glu Gln
1               5                   10                  15

Gly Gln Leu Leu Lys Ile Glu Glu Val Asn Ala Glu Pro Asp Leu
                20                  25                  30

Ala Ala Ala Ala Asn Ala Thr Gly Arg Ile Gly Asp Gly Ala Pro Ala
            35                  40                  45

Leu Trp Phe Asp Asn Ile Arg Gly Phe Thr Asp Ala Arg Val Val Met
    50                  55                  60

Asn Thr Ile Gly Ser Trp Gln Asn His Ala Ile Ser Met Gly Leu Pro
65                  70                  75                  80

Ala Asn Thr Pro Val Lys Lys Gln Ile Asp Glu Phe Ile Arg Arg Trp
                85                  90                  95

Asp Lys Phe Pro Val Ala Pro Glu Arg Arg Ala Asn Pro Ala Trp Ala
            100                 105                 110

Gln Asn Thr Val Asp Gly Glu Glu Ile Asn Leu Phe Asp Ile Leu Pro
        115                 120                 125

Leu Phe Arg Leu Asn Asp Gly Asp Gly Gly Phe Tyr Leu Asp Lys Ala
    130                 135                 140

Cys Val Val Ser Arg Asp Pro Leu Asp Pro Asp His Phe Gly Lys Gln
145                 150                 155                 160

Asn Val Gly Ile Tyr Arg Met Glu Val Lys Gly Lys Arg Lys Leu Gly
                165                 170                 175

Leu Gln Pro Val Pro Met His Asp Ile Ala Leu His Leu His Lys Ala
            180                 185                 190

Glu Glu Arg Gly Glu Asp Leu Pro Ile Ala Ile Thr Leu Gly Asn Asp
        195                 200                 205

Pro Ile Ile Thr Leu Met Gly Ala Thr Pro Leu Lys Tyr Asp Gln Ser
    210                 215                 220

Glu Tyr Glu Met Ala Gly Ala Leu Arg Glu Ser Pro Tyr Pro Ile Ala
225                 230                 235                 240

Thr Ala Pro Leu Thr Gly Phe Asp Val Pro Trp Gly Ser Glu Val Ile
                245                 250                 255

Leu Glu Gly Val Ile Glu Gly Arg Lys Arg Glu Ile Glu Gly Pro Phe
            260                 265                 270

Gly Glu Phe Thr Gly His Tyr Ser Gly Gly Arg Asn Met Thr Val Val
        275                 280                 285

Arg Ile Asp Lys Val Ser Tyr Arg Thr Lys Pro Ile Phe Glu Ser Leu
    290                 295                 300

Tyr Leu Gly Met Pro Trp Thr Glu Ile Asp Tyr Leu Met Gly Pro Ala
305                 310                 315                 320

```
Thr Cys Val Pro Leu Tyr Gln Gln Leu Lys Ala Glu Phe Pro Glu Val
            325                 330                 335

Gln Ala Val Asn Ala Met Tyr Thr His Gly Leu Leu Ala Ile Ile Ser
        340                 345                 350

Thr Lys Lys Arg Tyr Gly Gly Phe Ala Arg Ala Val Gly Leu Arg Ala
    355                 360                 365

Met Thr Thr Pro His Gly Leu Gly Tyr Val Lys Met Val Ile Met Val
370                 375                 380

Asp Glu Asp Val Asp Pro Phe Asn Leu Pro Gln Val Met Trp Ala Leu
385                 390                 395                 400

Ser Ser Lys Val Asn Pro Ala Gly Asp Leu Val Gln Leu Pro Asn Met
                405                 410                 415

Ser Val Leu Glu Leu Asp Pro Gly Ser Ser Pro Ala Gly Ile Thr Asp
            420                 425                 430

Lys Leu Ile Ile Asp Ala Thr Thr Pro Val Ala Pro Asp Asn Arg Gly
        435                 440                 445

His Tyr Ser Gln Pro Val Gln Asp Leu Pro Glu Thr Lys Ala Trp Ala
    450                 455                 460

Glu Lys Leu Thr Ala Met Leu Ala Ala Arg Gln
465                 470                 475
```

<210> SEQ ID NO 3
<211> LENGTH: 1195
<212> TYPE: DNA
<213> ORGANISM: Artificial
<220> FEATURE:
<223> OTHER INFORMATION: pCASE1-ori

<400> SEQUENCE: 3

| | | | | | |
|---|---|---|---|---|---|
| atgaaaaccg | accgtgcacg | ctcgtgtgag | aaagtcagct | acatgagacc | aactacccgc | 60 |
| cctgagggac | gctttgagca | gctgtggctg | ccgctgtggc | cattggcaag | cgatgacctc | 120 |
| cgtgagggca | tttaccgcac | ctcacggaag | aacgcgctgg | ataagcgcta | cgtcgaagcc | 180 |
| aatcccgacg | cgctctctaa | cctcctggtc | gttgacatcg | accaggagga | cgcgcttttg | 240 |
| cgctctttgt | gggacaggga | ggactggaga | cctaacgcgg | tggttgaaaa | ccccttaaac | 300 |
| gggcacgcac | acgctgtctg | ggcgctcgcg | gagccattta | cccgcaccga | atacgccaaa | 360 |
| cgcaagcctt | tggcctatgc | cgcggctgtc | accgaaggcc | tacggcgctc | tgtcgatggc | 420 |
| gatagcggat | actccgggct | gatcaccaaa | accccgagc | acactgcatg | ggatagtcac | 480 |
| tggatcaccg | ataagctgta | tacgctcgat | gagctgcgct | tttggctcga | agaaaccggc | 540 |
| tttatgccgc | ctgcgtcctg | gaggaaaacg | cggcggttct | cgccagttgg | tctaggtcgt | 600 |
| aattgcgcac | tctttgaaag | cgcacgtacg | tgggcatatc | gggaggtcag | aaagcatttt | 660 |
| ggagacgctg | acggcctagg | ccgcgcaatc | caaaccaccg | cgcaagcact | taaccaagag | 720 |
| ctgtttgatg | aaccactacc | tgtggccgaa | gttgactgta | ttgccaggtc | aatccataaa | 780 |
| tggatcatca | ccaagtcacg | catgtggaca | gacggcgccg | ccgtctacga | cgccacattc | 840 |
| accgcaatgc | aatccgcacg | cgggaagaaa | ggctggcaac | gaagcgctga | ggtgcgtcgt | 900 |
| gaggctggac | atactctttg | gaggaacatt | ggctaaggtt | tatgcacgtt | atccacgcaa | 960 |
| cggaaaaaca | gcccgcgagc | tggcagaacg | tgccggtatg | tcggtgagaa | cagctcaacg | 1020 |
| atggacttcc | gaaccgcgtg | aagtgttcat | taaacgtgcc | aacgagaagc | gtgctcgcgt | 1080 |
| ccaggagctg | cgcgccaaag | gtctgtccat | gcgcgctatc | gcggcagaga | ttggttgctc | 1140 |
| ggtgggcacg | gttcaccgct | acgtcaaaga | agttgaagag | aagaaaaccg | cgtaa | 1195 |

<210> SEQ ID NO 4
<211> LENGTH: 2675
<212> TYPE: DNA
<213> ORGANISM: Artificial
<220> FEATURE:
<223> OTHER INFORMATION: pHSG298

<400> SEQUENCE: 4

| | | | | | |
|---|---|---|---|---|---|
| gaggtctgcc | tcgtgaagaa | ggtgttgctg | actcatacca | ggcctgaatc | gccccatcat | 60 |
| ccagccagaa | agtgagggag | ccacggttga | tgagagcttt | gttgtaggtg | gaccagttgg | 120 |
| tgattttgaa | cttttgcttt | gccacggaac | ggtctgcgtt | gtcgggaaga | tgcgtgatct | 180 |
| gatccttcaa | ctcagcaaaa | gttcgattta | ttcaacaaag | ccacgttgtg | tctcaaaatc | 240 |
| tctgatgtta | cattgcacaa | gataaaaata | tatcatcatg | aacaataaaa | ctgtctgctt | 300 |
| acataaacag | taatacaagg | ggtgttatga | gccatattca | acgggaaacg | tcttgctcga | 360 |
| agccgcgatt | aaattccaac | atggatgctg | atttatatgg | gtataaatgg | gctcgcgata | 420 |
| atgtcgggca | atcaggtgcg | acaatctatc | gattgtatgg | gaagcccgat | gcgccagagt | 480 |
| tgtttctgaa | acatggcaaa | ggtagcgttg | ccaatgatgt | tacagatgag | atggtcagac | 540 |
| taaactggct | gacggaattt | atgcctcttc | cgaccatcaa | gcattttatc | cgtactcctg | 600 |
| atgatgcatg | gttactcacc | actgcgatcc | ccgggaaaac | agcattccag | gtattagaag | 660 |
| aatatcctga | ttcaggtgaa | aatattgttg | atgcgctggc | agtgttcctg | cgccggttgc | 720 |
| attcgattcc | tgtttgtaat | tgtcctttta | acagcgatcg | cgtatttcgt | ctcgctcagg | 780 |
| cgcaatcacg | aatgaataac | ggtttggttg | atgcgagtga | ttttgatgac | gagcgtaatg | 840 |
| gctggcctgt | tgaacaagtc | tggaaagaaa | tgcataagct | tttgccattc | tcaccggatt | 900 |
| cagtcgtcac | tcatggtgat | ttctcacttg | ataaccttat | ttttgacgag | gggaaattaa | 960 |
| taggttgtat | tgatgttgga | cgagtcggaa | tcgcagaccg | ataccaggat | cttgccatcc | 1020 |
| tatggaactg | cctcggtgag | ttttctcctt | cattacagaa | acggcttttt | caaaaatatg | 1080 |
| gtattgataa | tcctgatatg | aataaattgc | agtttcattt | gatgctcgat | gagtttttct | 1140 |
| aatcagaatt | ggttaattgg | ttgtaacact | ggcagagcat | tacgctgact | tgacgggacg | 1200 |
| gcggctttgt | tgaataaatc | gcattcgcca | ttcaggctgc | gcaactgttg | ggaagggcga | 1260 |
| tcggtgcggg | cctcttcgct | attacgccag | ctggcgaaag | gggatgtgc | tgcaaggcga | 1320 |
| ttaagttggg | taacgccagg | gttttcccag | tcacgacgtt | gtaaaacgac | ggccagtgcc | 1380 |
| aagcttgcat | gcctgcaggt | cgactctaga | ggatccccgg | gtaccgagct | cgaattcgta | 1440 |
| atcatgtcat | agctgtttcc | tgtgtgaaat | tgttatccgc | tcacaattcc | acacaacata | 1500 |
| cgagccggaa | gcataaagtg | taaagcctgg | ggtgcctaat | gagtgagcta | actcacatta | 1560 |
| attgcgttgc | gctcactgcc | cgctttccag | tcgggaaacc | tgtcgtgcca | gctgcattaa | 1620 |
| tgaatcggcc | aacgcgcggg | gagaggcggt | ttgcgtattg | gcgaacttt | gctgagttga | 1680 |
| aggatcagat | cacgcatctt | cccgacaacg | cagaccgttc | cgtggcaaag | caaaagttca | 1740 |
| aaatcagtaa | ccgtcagtgc | cgataagttc | aaagttaaac | ctggtgttga | taccaacatt | 1800 |
| gaaacgctga | tcgaaaacgc | gctgaaaaac | gctgctgaat | gtgcgagctt | cttccgcttc | 1860 |
| ctcgctcact | gactcgctgc | gctcggtcgt | tcggctgcgg | cgagcggtat | cagctcactc | 1920 |
| aaaggcggta | atacggttat | ccacagaatc | aggggataac | gcaggaaaga | acatgtgagc | 1980 |
| aaaaggccag | caaaaggcca | ggaaccgtaa | aaaggccgcg | ttgctggcgt | ttttccatag | 2040 |

```
gctccgcccc cctgacgagc atcacaaaaa tcgacgctca agtcagaggt ggcgaaaccc    2100
gacaggacta taaagatacc aggcgtttcc ccctggaagc tccctcgtgc gctctcctgt    2160
tccgaccctg ccgcttaccg gataccgtgtc cgccttttctc ccttcgggaa gcgtggcgct   2220
```

```
tccgaccctg ccgcttaccg gataccgtc cgccttttctc ccttcgggaa gcgtggcgct    2220
ttctcaatgc tcacgctgta ggtatctcag ttcggtgtag gtcgttcgct ccaagctggg    2280
ctgtgtgcac gaaccccccg ttcagcccga ccgctgcgcc ttatccggta actatcgtct    2340
tgagtccaac ccggtaagac acgacttatc gccactggca gcagccactg gtaacaggat    2400
tagcagagcg aggtatgtag gcggtgctac agagttcttg aagtggtggc ctaactacgg    2460
ctacactaga aggacagtat ttggtatctg cgctctgctg aagccagtta ccttcggaaa    2520
aagagttggt agctcttgat ccggcaaaca aaccaccgct ggtagcggtg ttttttttgt    2580
ttgcaagcag cagattacgc gcagaaaaaa aggatctcaa gaagatcctt tgatcttttc    2640
tacggggtct gacgctcagt ggaacgatcc gtcga                               2675

<210> SEQ ID NO 5
<211> LENGTH: 25
<212> TYPE: DNA
<213> ORGANISM: Artificial
<220> FEATURE:
<223> OTHER INFORMATION: PCR primer

<400> SEQUENCE: 5
atagatctag aacgtccgta ggagc                                           25

<210> SEQ ID NO 6
<211> LENGTH: 26
<212> TYPE: DNA
<213> ORGANISM: Artificial
<220> FEATURE:
<223> OTHER INFORMATION: PCR primer

<400> SEQUENCE: 6
atagatctga cttggttacg atggac                                          26

<210> SEQ ID NO 7
<211> LENGTH: 27
<212> TYPE: DNA
<213> ORGANISM: Artificial
<220> FEATURE:
<223> OTHER INFORMATION: PCR primer

<400> SEQUENCE: 7
atagatctag gtttcccgac tggaaag                                         27

<210> SEQ ID NO 8
<211> LENGTH: 28
<212> TYPE: DNA
<213> ORGANISM: Artificial
<220> FEATURE:
<223> OTHER INFORMATION: PCR primer

<400> SEQUENCE: 8
atagatctcg tgccagctgc attaatga                                        28

<210> SEQ ID NO 9
<211> LENGTH: 550
<212> TYPE: DNA
<213> ORGANISM: Corynebacterium glutamicum

<400> SEQUENCE: 9
cgaagatctg aagattcctg atacaaattc tgttgtgacg gaagatttgt tggaagaaat    60
```

```
ctagtcgctc gtctcataaa aacgaccgag cctattggga ttaccattga agccagtgtg    120
agttgcatca cactggcttc aaatctgaga ctttactttg tggattcacg ggggtgtagt    180
gcaattcata attagcccca ttcggggag cagatcgcgg cgcgaacgat ttcaggttcg     240
ttccctgcaa aaactattta gcgcaagtgt tggaaatgcc cccgtctggg gtcaatgtct    300 attttgaat gtgtttgtat gattttgaat ccgctgcaaa atctttgttt ccccgctaaa     360
gttggggaca ggttgacacg gagttgactc gacgaattat ccaatgtgag taggtttggt    420
gcgtgagttg gaaaatttcg ccatactcgc ccttgggttc tgtcagctca agaattcttg    480
agtgaccgat gctctgattg acctaactgc ttgacacatt gcatttccta caatctttag    540
aggagacaca                                                           550
```

<210> SEQ ID NO 10
<211> LENGTH: 425
<212> TYPE: DNA
<213> ORGANISM: Artificial
<220> FEATURE:
<223> OTHER INFORMATION: rrnBT1T2 terminator

<400> SEQUENCE: 10

```
ctgttttggc ggatgagaga agattttcag cctgatacag attaaatcag aacgcagaag    60
cggtctgata aaacagaatt tgcctggcgg cagtagcgcg gtggtcccac ctgaccccat    120
gccgaactca gaagtgaaac gccgtagcgc cgatggtagt gtggggtctc cccatgcgag    180
agtagggaac tgccaggcat caaataaaac gaaaggctca gtcgaaagac tgggcctttc    240
gttttatctg ttgtttgtcg gtgaacgctc tcctgagtag acaaatccg ccgggagcgg    300 atttgaacgt tgcgaagcaa cggcccggag ggtggcgggc aggacgcccg ccataaactg    360
ccaggcatca aattaagcag aaggccatcc tgacggatgg cctttttgcg tttctacaaa    420
ctctt                                                               425
```

<210> SEQ ID NO 11
<211> LENGTH: 31
<212> TYPE: DNA
<213> ORGANISM: Artificial
<220> FEATURE:
<223> OTHER INFORMATION: PCR primer

<400> SEQUENCE: 11

```
ctctgtcgac ccgaagatct gaagattcct g                                   31
```

<210> SEQ ID NO 12
<211> LENGTH: 46
<212> TYPE: DNA
<213> ORGANISM: Artificial
<220> FEATURE:
<223> OTHER INFORMATION: PCR primer

<400> SEQUENCE: 12

```
ctctgtcgac ggatccccat ggtgtgtctc tctaaagat tgtagg                    46
```

<210> SEQ ID NO 13
<211> LENGTH: 36
<212> TYPE: DNA
<213> ORGANISM: Artificial
<220> FEATURE:
<223> OTHER INFORMATION: PCR primer

<400> SEQUENCE: 13
ctctgcatgc ccatggctgt tttggcggat gagaga           36

<210> SEQ ID NO 14
<211> LENGTH: 41
<212> TYPE: DNA
<213> ORGANISM: Artificial
<220> FEATURE:
<223> OTHER INFORMATION: PCR primer

<400> SEQUENCE: 14
ctctgcatgc tcatgaaaga gtttgtagaa acgcaaaaag g      41

<210> SEQ ID NO 15
<211> LENGTH: 26
<212> TYPE: DNA
<213> ORGANISM: Artificial
<220> FEATURE:
<223> OTHER INFORMATION: PCR primer

<400> SEQUENCE: 15
ctctcatatg acagcatcac cttggg                      26

<210> SEQ ID NO 16
<211> LENGTH: 32
<212> TYPE: DNA
<213> ORGANISM: Artificial
<220> FEATURE:
<223> OTHER INFORMATION: PCR primer

<400> SEQUENCE: 16
ctctcatatg tcatcttaac gacgctccat tc               32

<210> SEQ ID NO 17
<211> LENGTH: 38
<212> TYPE: DNA
<213> ORGANISM: Artificial
<220> FEATURE:
<223> OTHER INFORMATION: PCR primer

<400> SEQUENCE: 17
ctctcatatg gtaaatgatc cttatgattt acgaaaag         38

<210> SEQ ID NO 18
<211> LENGTH: 28
<212> TYPE: DNA
<213> ORGANISM: Artificial
<220> FEATURE:
<223> OTHER INFORMATION: PCR primer

<400> SEQUENCE: 18
ctctcatatg ctaatctccc tcccaacg                    28

<210> SEQ ID NO 19
<211> LENGTH: 5118
<212> TYPE: DNA
<213> ORGANISM: Artificial
<220> FEATURE:
<223> OTHER INFORMATION: pCRB207

<400> SEQUENCE: 19
agatctaggt ttcccgactg gaaagcgggc agtgagcgca acgcaattaa tgtgagttag    60
ctcactcatt aggcacccca ggctttacac tttatgcttc cggctcgtat gttgtgtgga   120
attgtgagcg gataacaatt tcacacagga aacagctatg accatgatta cgaattcgag   180
ctcggtaccc ggggatcctc tagagtcgac ccgaagatct gaagattcct gatacaaatt   240

-continued

```
ctgttgtgac ggaagatttg ttggaagaaa tctagtcgct cgtctcataa aaacgaccga    300
gcctattggg attaccattg aagccagtgt gagttgcatc acactggctt caaatctgag    360
actttacttt gtggattcac gggggtgtag tgcaattcat aattagcccc attcggggga    420
gcagatcgcg gcgcgaacga tttcaggttc gttccctgca aaaactattt agcgcaagtg    480
ttggaaatgc ccccgtctgg ggtcaatgtc tattttgaa tgtgtttgta tgattttgaa      540
tccgctgcaa aatctttgtt tccccgctaa agttggggac aggttgacac ggagttgact    600
cgacgaatta tccaatgtga gtaggtttgg tgcgtgagtt ggaaaatttc gccatactcg    660
cccttgggtt ctgtcagctc aagaattctt gagtgaccga tgctctgatt gacctaactg    720
cttgacacat tgcatttcct acaatcttta gaggagacac accatggctg ttttggcgga    780
tgagagaaga ttttcagcct gatacagatt aaatcagaac gcagaagcgg tctgataaaa    840
cagaatttgc ctggcggcag tagcgcggtg gtcccacctg accccatgcc gaactcagaa    900
gtgaaacgcc gtagcgccga tggtagtgtg gggtctcccc atgcgagagt agggaactgc    960
caggcatcaa ataaaacgaa aggctcagtc gaaagactgg gcctttcgtt ttatctgttg    1020
tttgtcggtg aacgctctcc tgagtaggac aaatccgccg ggagcggatt tgaacgttgc    1080
gaagcaacgg cccggagggt ggcgggcagg acgcccgcca taaactgcca ggcatcaaat   1140
taagcagaag gccatcctga cggatggcct ttttgcgttt ctacaaactc tttcatgggg    1200
atccgtcgac ctgcaggcat gcaagcttgg cactggccgt cgttttacaa cgtcgtgact    1260
gggaaaaccc tggcgttacc caacttaatc gccttgcagc acatcccct ttcgccagct      1320 ggcgtaatag cgaagaggcc cgcaccgatc gcccttccca acagttgcgc agcctgaatg    1380
gcgaatgcga tttattcaac aaagccgccg tcccgtcaag tcagcgtaat gctctgccag    1440
tgttacaacc aattaaccaa ttctgattag aaaaactcat cgagcatcaa atgaaactgc    1500
aatttattca tatcaggatt atcaatacca tatttttgaa aaagccgttt ctgtaatgaa    1560
ggagaaaact caccgaggca gttccatagg atggcaagat cctggtatcg gtctgcgatt    1620
ccgactcgtc caacatcaat acaacctatt aatttcccct cgtcaaaaat aaggttatca    1680
agtgagaaat caccatgagt gacgactgaa tccggtgaga atggcaaaag cttatgcatt    1740
tctttccaga cttgttcaac aggccagcca ttacgctcgt catcaaaatc actcgcatca    1800
accaaaccgt tattcattcg tgattgcgcc tgagcgagac gaaatacgcg atcgctgtta    1860
aaaggacaat tacaaacagg aatcgaatgc aaccggcgca ggaacactgc cagcgcatca    1920
acaatatttt cacctgaatc aggatattct tctaatacct ggaatgctgt tttcccgggg    1980
atcgcagtgg tgagtaacca tgcatcatca ggagtacgga taaaatgctt gatggtcgga    2040
agaggcataa attccgtcag ccagtttagt ctgaccatct catctgtaac atcattggca    2100
acgctacctt tgccatgttt cagaaacaac tctggcgcat cgggcttccc atacaatcga    2160
tagattgtcg cacctgattg cccgacatta tcgcgagccc atttataccc atataaatca    2220
gcatccatgt tggaatttaa tcgcggcttc gagcaagacg tttcccgttg aatatggctc    2280
ataacacccc ttgtattact gtttatgtaa gcagacagtt ttattgttca tgatgatata    2340
tttttatctt gtgcaatgta acatcagaga ttttgagaca caacgtggct ttgttgaata    2400
aatcgaactt tgctgagtt gaaggatcag atcacgcatc ttcccgacaa cgcagaccgt    2460
tccgtggcaa agcaaaagtt caaaatcacc aactggtcca cctacaacaa agctctcatc    2520
aaccgtggct ccctcacttt ctggctggat gatggggcga ttcaggcctg gtatgagtca    2580
```

```
gcaacacctt cttcacgagg cagacctctc gacggagttc cactgagcgt cagaccccgt    2640
agaaaagatc aaaggatctt cttgagatcc ttttttctg cgcgtaatct gctgcttgca    2700
aacaaaaaaa ccaccgctac cagcggtggt ttgtttgccg gatcaagagc taccaactct    2760
ttttccgaag gtaactggct tcagcagagc gcagatacca aatactgttc ttctagtgta    2820
gccgtagtta ggccaccact tcaagaactc tgtagcaccg cctacatacc tcgctctgct    2880
aatcctgtta ccagtggctg ctgccagtgg cgataagtcg tgtcttaccg ggttggactc    2940
aagacgatag ttaccggata aggcgcagcg gtcgggctga acggggggtt cgtgcacaca    3000
gcccagcttg gagcgaacga cctacaccga actgagatac ctacagcgtg agctatgaga    3060
aagcgccacg cttcccgaag ggagaaaggc ggacaggtat ccggtaagcg gcagggtcgg    3120
aacaggagag cgcacgaggg agcttccagg gggaaacgcc tggtatcttt atagtcctgt    3180
cgggtttcgc cacctctgac ttgagcgtcg attttgtga tgctcgtcag ggggcggag    3240 cctatggaaa aacgccagca acgcggcctt tttacggttc ctggccttt gctggccttt    3300 tgctcacatg ttctttcctg cgttatcccc tgattctgtg gataaccgta ttaccgcctt    3360
tgagtgagct gataccgctc gccgcagccg aacgaccgag cgcagcgagt cagtgagcga    3420
ggaagcggaa gaagctcgca cattcagcag cgttttcag cgcgttttcg atcaacgttt    3480
caatgttggt atcaacacca ggtttaactt tgaacttatc ggcactgacg gttactgatt    3540
ttgaactttt gctttgccac ggaacggtct gcgttgtcgg gaagatgcgt gatctgatcc    3600
ttcaactcag caaaagttcg ccaatacgca aaccgcctct ccccgcgcgt tggccgattc    3660
attaatgcag ctggcacgag atctgacttg gttacgatgg actttgaaca cgccgagggt    3720
gactaaaccg ctggatttac gcggttttct tctcttcaac ttctttgacg tagcggtgaa    3780
ccgtgcccac cgagcaacca atctctgccg cgatagcgcg catggacaga cctttggcgc    3840
gcagctcctg gacgcgagca cgcttctcgt tggcacgttt aatgaacact tcacgcggtt    3900
cggaagtcca tcgttgagct gttctcaccg acataccggc acgttctgcc agctcgcggg    3960 ctgttttcc gttgcgtgga taacgtgcat aaaccttagc caatgttcct ccaaagagta    4020
tgtccagcct cacgacgcac ctcagcgctt cgttgccagc ctttcttccc gcgtgcggat    4080
tgcattgcgg tgaatgtggc gtcgtagacg gcggcgccgt ctgtccacat gcgtgacttg    4140
gtgatgatcc atttatggat tgacctggca atacagtcaa cttcggccac aggtagtggt    4200
tcatcaaaca gctcttggtt aagtgcttgc gcggtggttt ggattgcgcg gcctaggccg    4260
tcagcgtctc caaaatgctt tctgacctcc cgatatgccc acgtacgtgc gctttcaaag    4320
agtgcgcaat tacgacctag accaactggc gagaaccgcc gcgttttcct ccaggacgca    4380
ggcggcataa agccggtttc ttcgagccaa aagcgcagct catcgagcgt atacagctta    4440
tcggtgatcc agtgactatc ccatgcagtg tgctcggggt ttttggtgat cagcccggag    4500
tatccgctat cgccatcgac agagcgccgt aggccttcgg tgacagccgc ggcataggcc    4560
aaaggcttgc gtttggcgta ttcggtgcgg gtaaatggct ccgcgagcgc ccagacagcg    4620
tgtgcgtgcc cgtttaaggg gttttcaacc accgcgttag gtctccagtc ctccctgtcc    4680
cacaaagagc gcaaaagcgc gtcctcctgg tcgatgtcaa cgaccaggag gttagagagc    4740
gcgtcgggat tggcttcgac gtagcgctta tccagcgcgt tcttccgtga ggtgcggtaa    4800
atgccctcac ggaggtcatc gcttgccaat ggccacagcg gcagccacag ctgctcaaag    4860
cgtccctcag ggcgggtagt tggtctcatg tagctgactt tctcacacga gcgtgcacgg    4920 tcggtttttca ttcataatac gacatttaac caagtcagat gtttccccgg tttccggggg    4980
```

```
ttcccctgaa gaacccttcc agtgcgagcg aagcgagctc ctttggccgg cgcccctcag    5040
gtagccctct aaggctccca gggctccgcc cctccctgag gttggctcaa gcctcctggt    5100
ggctcctacg gacgttct                                                  5118
```

<210> SEQ ID NO 20
<211> LENGTH: 29
<212> TYPE: DNA
<213> ORGANISM: Artificial
<220> FEATURE:
<223> OTHER INFORMATION: PCR primer

<400> SEQUENCE: 20

```
ctctcatatg ctgttttggc ggatgagag                                        29
```

<210> SEQ ID NO 21
<211> LENGTH: 33
<212> TYPE: DNA
<213> ORGANISM: Artificial
<220> FEATURE:
<223> OTHER INFORMATION: PCR primer

<400> SEQUENCE: 21

```
ctctcatatg gtgtctcctc taaagattgt agg                                   33
```

<210> SEQ ID NO 22
<211> LENGTH: 23
<212> TYPE: DNA
<213> ORGANISM: Artificial
<220> FEATURE:
<223> OTHER INFORMATION: PCR primer

<400> SEQUENCE: 22

```
ctctcatatg aacgggccgg aac                                              23
```

<210> SEQ ID NO 23
<211> LENGTH: 29
<212> TYPE: DNA
<213> ORGANISM: Artificial
<220> FEATURE:
<223> OTHER INFORMATION: PCR primer

<400> SEQUENCE: 23

```
ctctcatatg tcaatcatcc accccgaag                                        29
```

<210> SEQ ID NO 24
<211> LENGTH: 2252
<212> TYPE: DNA
<213> ORGANISM: Enterobacter cloacae

<400> SEQUENCE: 24

```
atgagattga tcgtgggaat gacgggagca acaggtgctc cgctgggtgt ggctttactg     60
caggcgttac gtgacatgcc agaggttgaa acccatctgg tgatgtcgaa atgggcgaaa    120
accaccattg agctggaaac gccttatacc gcgcaggatg tcgccgccct ggcagatgtc    180
gttcacagtc ctgccgatca ggctgccacc atctcctccg gctcgtttcg taccgacggc    240
atgatcgtca ttccctgcag catgaaaacg ctggcgggta tccgcgcggg ctatgccgaa    300
gggctggtgg gccgtgcggc agacgtggtg ctgaaagagg ggcgcaagct ggtgctggtc    360
ccgcgtgaaa cgccgctcag caccattcat ctggagaaca tgctcgcgct ttcccgcatg    420
ggggtggcga tggtgccgcc catgcctgcg tattacaacc cccgcaaac cgccgatgat    480
```

```
atcacccagc atatcgtgac ccgcgtactc gaccagtttg gtctggagca caaaaaggcg    540
cgtcgctgga acggcctgca ggcggcgaaa cattttttcac aggagaataa cgatggcatt    600
tgatgatttg agaagcttcc tgcaggcgct agatgagcaa gggcaactgc tgaaaattga    660
agaagaggtc aatgcggagc cggatctggc ggcggccgct aacgcgacgg gacgtatcgg    720
tgatggtgcg cctgcgctgt ggttcgataa cattcgcggg tttaccgatg ccagggtggt    780
gatgaacacc atcggctcct ggcagaacca cgccatttcg atggggctgc cggcgaatac    840
cccggtcaaa aagcagatcg atgagtttat tcgccgctgg gataaattcc cggtcgcacc    900
ggagcgccgg gccaaccccg catgggcgca gaatacggtg gacggtgagg agattaacct    960
gttcgacatc ctgccgctgt ttcgcctgaa cgacgggac ggcggttttt atctcgacaa    1020
agcgtgcgtt gtctcgcgcg atccgctcga cccggaccat ttcggcaagc agaacgtcgg    1080
tatttaccgc atggaagtga agggcaaacg taagctcggc ctgcagccgg tgccgatgca    1140
tgatatcgcc ctgcatctgc ataaagccga agagcgtggt gaagacctgc cgattgcgat    1200
tacgttgggc aacgatccga tcatcaccct gatgggcgca acgccgctga aatacgatca    1260
gtccgagtat gaaatggccg gggcgctgcg tgaaagcccg tacccgattg cgaccgcgcc    1320
gttgaccggc ttcgatgtgc cgtggggtc tgaagtgatc ctggaagggg tgattgaagg    1380
ccgtaaacgt gaaattgaag gccgttcgg tgagtttacc gggcactatt cgggcggacg    1440
caatatgacg gtggtccgta ttgataaagt ctcgtaccgc accaaaccga ttttcgaatc    1500
cctctatctc gggatgccct ggaccgagat cgactacctg atggggccag ccacctgtgt    1560
gccgctttac cagcaactga aagcggagtt ccctgaagtg caggcggtga acgcgatgta    1620
tacccacggt ctgctggcga tcatctccac caaaaaacgc tacggtggtt ttgcccgcgc    1680
ggtcggttta cgcgccatga ccacgccgca tggcctgggc tatgtgaaga tggtgattat    1740
ggtggatgaa gatgtcgatc cgttcaacct gccgcaggtg atgtgggcgc tgtcatcaaa    1800
agtgaacccg gcagggggatc tggtgcagct gccgaacatg tcggttcttg agcttgatcc    1860
tgggtccagc ccggcaggca tcaccgacaa gctgattatt gatgccacca cgcctgttgc    1920
gccggataac cgcggtcact acagccagcc ggtgcaggat ttacctgaaa ccaaagcctg    1980
ggctgaaaag ctgactgcga tgctggcagc acgccaataa ggaggaaaag atgatttgtc    2040
cacgttgtgc cgatgagcaa attgaggtga tggccacatc accggtgaaa gggatctgga    2100
cggtttatca gtgccagcat tgcctgtata cctggcgcga tactgagccg ctgcgtcgta    2160
ccagccgcga acattaccct gaagcgttcc gcatgacgca aaggatatt gatgaggcgc    2220
cgcaggtacc gaccattccg ccattgctgt aa                                 2252
```

```
<210> SEQ ID NO 25
<211> LENGTH: 30
<212> TYPE: DNA
<213> ORGANISM: Artificial
<220> FEATURE:
<223> OTHER INFORMATION: PCR primer

<400> SEQUENCE: 25
ctctcatatg agattgatcg tgggaatgac                                      30

<210> SEQ ID NO 26
<211> LENGTH: 30
<212> TYPE: DNA
<213> ORGANISM: Artificial
<220> FEATURE:
<223> OTHER INFORMATION: PCR primer
```

```
<400> SEQUENCE: 26
ctctcatatg ttacagcaat ggcggaatgg                                           30

<210> SEQ ID NO 27
<211> LENGTH: 26
<212> TYPE: DNA
<213> ORGANISM: Artificial
<220> FEATURE:
<223> OTHER INFORMATION: PCR primer

<400> SEQUENCE: 27
gtcgctccca tatgagattg atcgtg                                               26

<210> SEQ ID NO 28
<211> LENGTH: 26
<212> TYPE: DNA
<213> ORGANISM: Artificial
<220> FEATURE:
<223> OTHER INFORMATION: PCR primer

<400> SEQUENCE: 28
gctcctgcca tatgttacag caatgg                                               26

<210> SEQ ID NO 29
<211> LENGTH: 27
<212> TYPE: DNA
<213> ORGANISM: Artificial
<220> FEATURE:
<223> OTHER INFORMATION: P309R Primer Fwd

<400> SEQUENCE: 29
gggatgcgct ggaccgagat cgactac                                              27

<210> SEQ ID NO 30
<211> LENGTH: 27
<212> TYPE: DNA
<213> ORGANISM: Artificial
<220> FEATURE:
<223> OTHER INFORMATION: P309R Primer Rev

<400> SEQUENCE: 30
ggtccagcgc atcccgagat agaggga                                              27

<210> SEQ ID NO 31
<211> LENGTH: 27
<212> TYPE: DNA
<213> ORGANISM: Artificial
<220> FEATURE:
<223> OTHER INFORMATION: P309S Primer Fwd

<400> SEQUENCE: 31
gggatgtcct ggaccgagat cgactac                                              27

<210> SEQ ID NO 32
<211> LENGTH: 27
<212> TYPE: DNA
<213> ORGANISM: Artificial
<220> FEATURE:
<223> OTHER INFORMATION: P309S Primer Rev

<400> SEQUENCE: 32
ggtccaggac atcccgagat agaggga                                              27

<210> SEQ ID NO 33
```

```
<211> LENGTH: 27
<212> TYPE: DNA
<213> ORGANISM: Artificial
<220> FEATURE:
<223> OTHER INFORMATION: P309M Primer Fwd

<400> SEQUENCE: 33
gggatgatgt ggaccgagat cgactac                                              27

<210> SEQ ID NO 34
<211> LENGTH: 27
<212> TYPE: DNA
<213> ORGANISM: Artificial
<220> FEATURE:
<223> OTHER INFORMATION: P309M Primer Rev

<400> SEQUENCE: 34
ggtccacatc atcccgagat agaggga                                              27

<210> SEQ ID NO 35
<211> LENGTH: 27
<212> TYPE: DNA
<213> ORGANISM: Artificial
<220> FEATURE:
<223> OTHER INFORMATION: P309V Primer Fwd

<400> SEQUENCE: 35
gggatggtgt ggaccgagat cgactac                                              27

<210> SEQ ID NO 36
<211> LENGTH: 27
<212> TYPE: DNA
<213> ORGANISM: Artificial
<220> FEATURE:
<223> OTHER INFORMATION: P309V Primer Rev

<400> SEQUENCE: 36
ggtccacacc atcccgagat agaggga                                              27

<210> SEQ ID NO 37
<211> LENGTH: 27
<212> TYPE: DNA
<213> ORGANISM: Artificial
<220> FEATURE:
<223> OTHER INFORMATION: P309Q Primer Fwd

<400> SEQUENCE: 37
gggatgcagt ggaccgagat cgactac                                              27

<210> SEQ ID NO 38
<211> LENGTH: 27
<212> TYPE: DNA
<213> ORGANISM: Artificial
<220> FEATURE:
<223> OTHER INFORMATION: P309Q Primer Rev

<400> SEQUENCE: 38
ggtccactgc atcccgagat agaggga                                              27

<210> SEQ ID NO 39
<211> LENGTH: 27
<212> TYPE: DNA
<213> ORGANISM: Artificial
<220> FEATURE:
<223> OTHER INFORMATION: P309A Primer Fwd

<400> SEQUENCE: 39
```

```
gggatggcat ggaccgagat cgactac                                          27
```

<210> SEQ ID NO 40
<211> LENGTH: 27
<212> TYPE: DNA
<213> ORGANISM: Artificial
<220> FEATURE:
<223> OTHER INFORMATION: P309A Primer Rev

<400> SEQUENCE: 40

```
ggtccatgcc atcccgagat agaggga                                          27
```

<210> SEQ ID NO 41
<211> LENGTH: 27
<212> TYPE: DNA
<213> ORGANISM: Artificial
<220> FEATURE:
<223> OTHER INFORMATION: P309F Primer Fwd

<400> SEQUENCE: 41

```
gggatgttct ggaccgagat cgactac                                          27
```

<210> SEQ ID NO 42
<211> LENGTH: 27
<212> TYPE: DNA
<213> ORGANISM: Artificial
<220> FEATURE:
<223> OTHER INFORMATION: P309F Primer Rev

<400> SEQUENCE: 42

```
ggtccagaac atcccgagat agaggga                                          27
```

<210> SEQ ID NO 43
<211> LENGTH: 197
<212> TYPE: PRT
<213> ORGANISM: Enterobacter cloacae

<400> SEQUENCE: 43

```
Met Arg Leu Ile Val Gly Met Thr Gly Ala Thr Gly Ala Pro Leu Gly
1               5                   10                  15

Val Ala Leu Leu Gln Ala Leu Arg Asp Met Pro Glu Val Glu Thr His
                20                  25                  30

Leu Val Met Ser Lys Trp Ala Lys Thr Thr Ile Glu Leu Glu Thr Pro
            35                  40                  45

Tyr Thr Ala Gln Asp Val Ala Ala Leu Ala Asp Val Val His Ser Pro
        50                  55                  60

Ala Asp Gln Ala Ala Thr Ile Ser Ser Gly Ser Phe Arg Thr Asp Gly
65                  70                  75                  80

Met Ile Val Ile Pro Cys Ser Met Lys Thr Leu Ala Gly Ile Arg Ala
                85                  90                  95

Gly Tyr Ala Glu Gly Leu Val Gly Arg Ala Ala Asp Val Val Leu Lys
                100                 105                 110

Glu Gly Arg Lys Leu Val Leu Val Pro Arg Glu Thr Pro Leu Ser Thr
            115                 120                 125

Ile His Leu Glu Asn Met Leu Ala Leu Ser Arg Met Gly Val Ala Met
        130                 135                 140

Val Pro Pro Met Pro Ala Tyr Tyr Asn His Pro Gln Thr Ala Asp Asp
145                 150                 155                 160

Ile Thr Gln His Ile Val Thr Arg Val Leu Asp Gln Phe Gly Leu Glu
                165                 170                 175
```

```
His Lys Lys Ala Arg Arg Trp Asn Gly Leu Gln Ala Ala Lys His Phe
            180                 185                 190

Ser Gln Glu Asn Asn
        195

<210> SEQ ID NO 44
<211> LENGTH: 73
<212> TYPE: PRT
<213> ORGANISM: Enterobacter cloacae

<400> SEQUENCE: 44

Met Ile Cys Pro Arg Cys Ala Asp Glu Gln Ile Glu Val Met Ala Thr
1               5                   10                  15

Ser Pro Val Lys Gly Ile Trp Thr Val Tyr Gln Cys Gln His Cys Leu
            20                  25                  30

Tyr Thr Trp Arg Asp Thr Glu Pro Leu Arg Arg Thr Ser Arg Glu His
            35                  40                  45

Tyr Pro Glu Ala Phe Arg Met Thr Gln Lys Asp Ile Asp Glu Ala Pro
        50                  55                  60

Gln Val Pro Thr Ile Pro Pro Leu Leu
65                  70
```

CORYNEFORM BACTERIUM TRANSFORMANT WITH IMPROVED ANILINE PRODUCTIVITY AND PROCESS FOR PRODUCING ANILINE USING THE SAME

TECHNICAL FIELD

The present invention relates to a mutant enzyme having an improved aniline productivity, and provides a coryneform bacterium transformant constructed by specific gene recombination which uses the mutant to impart an aniline-producing function, and an efficient aniline-producing process using the transformant.

BACKGROUND ART

In order to solve recent problems of exhaustion and price increase of fossil resources and global warming, a process for producing chemical products without dependence on fossil resources has been desired. As a solution to such problems, biorefinery technology utilizing biomass resources, in particular inedible biomass resources as raw materials, has attracted keen attention.

Aniline is widely used as a starting raw material for the synthesis of dyes; functional polymers; chemical agents for tire rubber, including a vulcanization accelerator and an antioxidant; agricultural chemicals; medicinal drugs; or the like.

Currently, aniline is produced by chemical conversion from crude oil as a raw material. Specifically, benzene obtained from naphtha obtainable by distillation separation of crude oil is used as the raw material. More specifically, a process in which nitrobenzen obtained by nitration of benzene and a metal catalyst, such as copper or nickel, are used; a process in which nitrobenzen is hydrogenated by reduction using iron and hydrochloric acid; or a process in which chlorobenzene and ammonia are reacted at high temperature and pressure may be used.

However, these methods depend on fossil materials for benzene as the starting material, and in addition, need high-temperature and high-pressure conditions in the reaction process, causing problems of consumption of an enormous amount of fossil fuel and emissions of greenhouse gases, such as carbon dioxide. For the reason, the development of an environment-conscious bioprocess which uses renewable resources as raw materials and does not depend on fossil resources for the raw materials in the production process has been desired.

For bioprocess production of an aromatic compound, such as aniline, a synthetic pathway called shikimate pathway possessed by microorganisms and plants can be used. However, such a process, which consists of a great many reaction steps for the metabolism of raw material sugars, is less productive.

Further, when aniline is produced by a bioprocess, due to the cytotoxicity, the bacterial growth inhibitory effect, etc. of the produced aniline, the bacterial growth per se is inhibited. Therefore, industrial production of aniline by a bioprocess is very difficult.

Aniline production technologies using non-genetically-modified bacteria that have been disclosed so far include an example where aniline was produced by adding 4-aminobenzoic acid to *Mycobacterium smegmatis* (Non Patent Literature 1), and an example where aniline was produced by adding anthranilic acid or 4-aminobenzoic acid to virulent *Escherichia coli* O111:B4 cells or extracts thereof (Non Patent Literature 2).

However, in these documents, no enzyme molecule or enzyme gene involved in the aniline production was specified, and no later reports have been made. Non Patent Literature 1 reported aniline production from 7.3 mM 4-aminobenzoic acid, but whether the substance identification was correct or not is uncertain because the produced aniline was only a slight amount (6.9 $\mu$M in concentration) and the identification was performed based on comparison using paper chromatography.

The process of Non Patent Literature 2 is not suitable for industrial production because the microorganism used therein is virulent. In addition, the aniline identification is indirectly performed based on diazo coloring, and whether the substance identification was correct or not is also uncertain. Further, aniline generally inhibits the growth of the microorganism due to its cytotoxicity, and therefore production of high levels of aniline is rather difficult.

The present inventors have already found that a transformant constructed by introducing a gene which is derived from *Enterobacter cloacae* and which encodes an enzyme having aminobenzoate decarboxylase activity into a coryneform bacterium as a host produces 1.25 mM aniline from 5 mM 4-aminobenzoic acid (Patent Literature 1). However, for cost reduction in industrial production, the production of higher levels of aniline is required, and therefore the aminobenzoate decarboxylase activity needs to be further improved.

CITATION LIST

Patent Literature

[PTL 1] WO 2012/090978

Non Patent Literature

[NPL 1] The Journal of Biological Chemistry, Vol. 193, 453-458(1951)
[NPL 2] Journal of the American Chemical Society, Vol. 79, 628-630 (1957)

SUMMARY OF INVENTION

Technical Problem

An objective of the present invention is to provide an enzyme capable of efficiently converting aniline from aminobenzoic acid, a gene which encodes the enzyme, a microorganism having the gene introduced thereinto and being capable of efficiently producing aniline from aminobenzoic acid, and a process for efficiently producing aniline using the microorganism.

Solution to Problem

The present inventors found that a transformant constructed by introducing a gene which encodes aminobenzoate decarboxylase derived from *Enterobacter cloacae* into a coryneform bacterium can efficiently produce aniline from aminobenzoic acid.

The present inventors have wholeheartedly carried out investigations in order to achieve the objective of further improving the aniline productivity of the 4-hydroxybenzoate decarboxylase derived from *Enterobacter cloacae*. As a result, the inventors found out a mutant having threonine (T) in place of proline (P) at position 309 from the N terminus, and found that a transformant constructed by introducing a gene which encodes the mutant into a coryneform bacterium has an improved aniline productivity.

In addition, the inventors found that a transformant constructed by introducing a gene which encodes a site-specific mutant having any one of methionine (M), valine (V), glutamine (Q), serine (S), and arginine (R) in place of proline (P) at position 309 from the N terminus into a coryneform bacterium has a further improved aniline productivity, and completed the present invention.

Also, the inventors found the following fact: when *Escherichia coli*, which is widely used as a host for genetic modification, is aerobically cultured in the presence of aniline, the growth of *Escherichia coli* is greatly affected at an aniline level of 20 mM or higher; in contrast, in aerobic culture of a coryneform bacterium known as an amino-acid producing bacterium, the bacterium can grow even at an aniline level increased up to 60 mM. That is, the inventors found that a coryneform bacterium has a higher resistance to aniline than *Escherichia coli* widely used as a host for genetic modification, and thus is superior in the industrial aniline productivity (FIG. 2, FIG. 3).

That is, the present invention relates to the following.

[1] An aniline-producing transformant constructed by introducing a gene which encodes an enzyme having aminobenzoate decarboxylase activity into a coryneform bacterium as a host, characterized in that the enzyme having aminobenzoate decarboxylase activity is composed of an amino acid sequence which is the same as that represented by SEQ ID NO: 2 except for having a mutation of at least proline (P) at position 309 from the N terminus.

[2] The transformant of the above [1], wherein the mutation is replacement of the proline (P) at position 309 from the N terminus by one or more amino acids selected from the group consisting of methionine (M), valine (V), glutamine (Q), threonine (T), serine (S), and arginine (R).

[3] The transformant of the above [1] or [2], wherein the mutation is replacement of the proline (P) at position 309 from the N terminus by one or more amino acids selected from the group consisting of methionine (M), valine (V), and glutamine (Q).

[4] The transformant of anyone of the above [1] to [3], wherein the gene which encodes an enzyme having aminobenzoate decarboxylase activity is a gene derived from *Enterobacter cloacae*.

[5] The transformant of anyone of the above [1] to [4], wherein the coryneform bacterium as the host is *Corynebacterium glutamicum*.

[6] The transformant of the above [5], wherein the coryneform bacterium as the host is *Corynebacterium glutamicum* R (FERM P-18976 (FERM BP-18976)), ATCC13032, or ATCC13869.

[7] *Corynebacterium glutamicum* ANI-13 (Accession Number: NITE P-01583 (NITE BP-01583)), *Corynebacterium glutamicum* ANI-14 (Accession Number: NITE P-01584 (NITE BP-01584)), or *Corynebacterium glutamicum* ANI-15 (Accession Number: NITE P-01585 (NITE BP-01585)), each of which is a transformant of *Corynebacterium glutamicum*.

[8] A process for producing aniline, which comprises a step of allowing the transformant of any one of the above [1] to [7] to react in a reaction mixture containing aminobenzoic acid, an ester thereof, and/or a salt thereof under reducing conditions, and a step of recovering aniline from the reaction mixture.

[9] The process of the above [8], wherein the transformant does not substantially grow in the reaction step.

[10] The process of the above [8] or [9], wherein the oxidation-reduction potential of the reaction mixture under reducing conditions is −200 mV to −500 mV.

Advantageous Effects of Invention

Using the transformant constructed by introducing a gene which encodes a mutant of the present invention into a coryneform bacterium, aniline can be efficiently produced from aminobenzoic acid, an ester thereof, and/or a salt thereof.

DESCRIPTION OF EMBODIMENTS

Figure 1:
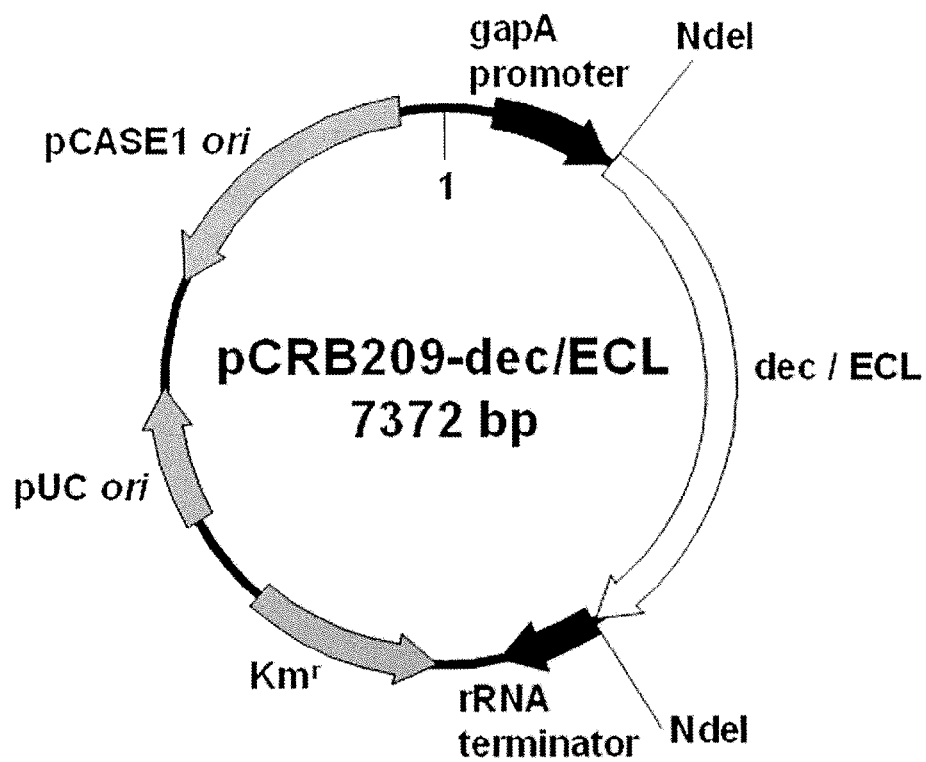
FIG. 1 shows the construct of the plasmid used in Production Example 1.

Hereinafter, the present invention will be described in detail.

An aspect of the present invention is an aniline-producing transformant constructed by introducing a gene which encodes an enzyme having aminobenzoate decarboxylase activity into a coryneform bacterium as a host, the enzyme being composed of an amino acid sequence which is the same as that represented by SEQ ID NO: 2 except for having a mutation of at least proline (P) at position 309 from the N terminus.

Host

The coryneform bacterium is a group of microorganisms defined in Bergey's Manual of Determinative Bacteriology, Vol. 8, 599 (1974), and is not particularly limited as long as it grows under normal aerobic conditions.

The specific examples include *Corynebacterium, Brevibacterium, Arthrobacter, Mycobacterium* and *Micrococcus*. Among the coryneform bacteria, *Corynebacterium* is preferred.

Examples of the *Corynebacterium* include *Corynebacterium glutamicum, Corynebacterium efficiens, Corynebacterium ammoniagenes, Corynebacterium halotolerance*, and *Corynebacterium alkanolyticum*. Inter alia, *Corynebacterium glutamicum* is preferred for safety and high aniline production. Examples of preferred strains include *Corynebacterium glutamicum* R (FERM P-18976 (International Accession No.: FERM BP-18976)), ATCC13032, ATCC13869, ATCC13058, ATCC13059, ATCC13060, ATCC13232, ATCC13286, ATCC13287, ATCC13655, ATCC13745, ATCC13746, ATCC13761, ATCC14020, ATCC31831, MJ-233 (FERM BP-1497), and MJ-233AB-41 (FERM BP-1498). Inter alia, strains R (FERM P-18976 (International Accession No.: FERM BP-18976)), ATCC13032, and ATCC13869 are preferred.

According to molecular biological classification, names of some species of coryneform bacteria, such as *Brevibacterium flavum, Brevibacterium lactofermentum, Brevibacterium divaricatum*, and *Corynebacterium lilium* are standardized to *Corynebacterium glutamicum* (Liebl, W. et al., Transfer of *Brevibacterium divaricatum* DSM 20297T, "*Brevibacterium flavum*" DSM 20411, "*Brevibacterium lactofermentum*" DSM 20412 and DSM 1412, and *Corynebacterium glutamicum* and their distinction by rRNA gene restriction patterns. Int. J. Syst. Bacteriol. 41: 255-260. (1991); and Kazuo Komagata et al., "Classification of the coryneform group of bacteria", Fermentation and industry, 45: 944-963 (1987)).

*Brevibacterium lactofermentum* ATCC13869, *Brevibacterium flavum* MJ-233 (FERM BP-1497) and MJ-233AB-41 (FERM BP-1498), etc. of the old classification are also suitable as *Corynebacterium glutamicum*.

Examples of the *Brevibacterium* include *Brevibacterium ammoniagenes* (for example, ATCC6872).

Examples of the *Arthrobacter* include *Arthrobacter globiformis* (for example, ATCC8010, ATCC4336, ATCC21056, ATCC31250, ATCC31738 and ATCC35698).

Examples of the *Mycobacterium* include *Mycobacterium bovis* (for example, ATCC19210 and ATCC27289).

Examples of the *Micrococcus* include *Micrococcus freudenreichii* (for example, NO. 239 (FERM P-13221)), *Micrococcus leuteus* (for example, NO. 240 (FERM P-13222)), *Micrococcus ureae* (for example, IAM1010), and *Micrococcus roseus* (for example, IFO3764).

The coryneform bacteria may be, let alone a wild type, a mutant thereof or an artificial recombinant thereof. Examples thereof include disruptants in which a gene of lactate dehydrogenase, phosphoenolpyruvate carboxylase, or malate dehydrogenase is disrupted. Using such a disruptant as a host can improve aniline productivity and reduce production of by-products.

Inter alia, preferred is a disruptant in which a lactate dehydrogenase gene is disrupted. In the disruptant, the lactate dehydrogenase gene is disrupted and the metabolic pathway from pyruvic acid to lactic acid is blocked. Inter alia, especially preferred is a disruptant of *Corynebacterium glutamicum* R (FERM P-18976 (International Accession No.: FERM BP-18976)) in which the lactate dehydrogenase gene is disrupted.

Such a disruptant can be prepared based on a conventional gene engineering process. Such a lactate dehydrogenase disruptant and the preparation process thereof are described in WO 2005/010182 A1.

Compared with other bacteria, coryneform bacteria are more resistant to solvents, such as aniline. Further, compared with other aerobic bacteria, coryneform bacteria more efficiently produce substances under reducing conditions where growth is substantially inhibited. In these respects, coryneform bacteria are suitable for the aniline production by the method of the present invention.

Aminobenzoate Decarboxylase

Aminobenzoate decarboxylase is an enzyme that catalyzes a reaction in which aniline is produced by elimination of carbonic acid from aminobenzoic acid and the reverse reaction.

The gene which encodes an enzyme having aminobenzoate decarboxylase activity is preferably derived from *Enterobacter cloacae*. In particular, when the substrate is 4-aminobenzoic acid, preferred is derived from *Enterobacter cloacae*.

Examples of the gene derived from *Enterobacter cloacae* used in the present invention include a DNA having a modified base sequence of SEQ ID NO: 1 encoding an amino acid sequence which is the same as that encoded by SEQ ID NO: 1 except for having at least a mutation of proline (P) at position 309 from the N terminus and has aminobenzoate decarboxylase activity (hereinafter "mutated base sequence"). The mutation means replacement, deletion, insertion, and/or addition of one to several amino acids. The "several" is not particularly limited and is usually 2 to 8, preferably 2 to 6, and more preferably 2 to 3. Preferred examples of the gene include a DNA having the above-described modified base sequence wherein the mutation in the encoded amino acid sequence is replacement of the proline (P) by at least one kind of amino acid other than proline, and the encoded amino acid sequence has aminobenzoate decarboxylase activity.

Examples of the enzyme having aminobenzoate decarboxylase activity derived from *Enterobacter cloacae* include a mutant having an amino acid sequence which is the same as that represented by SEQ ID NO: 2 except for having a mutation of at least proline (P) at position 309 from the N terminus. The mutant of the present invention is not particularly limited as long as it has aminobenzoate decarboxylase activity, and includes one having an introduced mutation of proline (P) at position 309 from the N terminus. The mutation means replacement, deletion, insertion, and/or addition of one to several amino acids. The "several" is not particularly limited and is usually 2 to 8, preferably 2 to 6, and more preferably 2 to 3. The mutant is not particularly limited, and a preferable example thereof is an enzyme having an amino acid sequence which is the same as that represented by SEQ ID NO: 2 except for having replacement of at least the proline (P) by one or more amino acids selected from the group consisting of methionine (M), valine (V), glutamine (Q), threonine (T), serine (S), and arginine (R), and a more preferable example is an enzyme having an amino acid sequence which is the same as that represented by SEQ ID NO: 2 except for having replacement of at least the proline (P) by one or more amino acids selected from the group consisting of methionine (M), valine (V), and glutamine (Q).

In the present invention, a DNA which hybridizes to a DNA consisting of a complementary base sequence of a base sequence comprising the above-described mutation under stringent conditions and which encodes a polypeptide having aminobenzoate decarboxylase activity can also be used. The "stringent conditions" as used herein means general conditions, for example, the conditions described in Molecular Cloning, A Laboratory Manual, Second edition, 1989, Vol. 2, p. 11. 45. It means, in particular, conditions where hybridization occurs at a temperature 5 to 10° C. below the melting temperature (Tm) of a perfect hybrid (for example, in 0.1% SDS and 0.5×SSC at 65 to 68° C. for 15 min, twice).

The aminobenzoate decarboxylase activity can be measured by a modified method of the method described in J. Am. Chem. Soc., 79, 628-630 (1957). Briefly, a coryneform bacterium is cultured in a nutrient medium at 33° C. for 18 hours, washed with minimal medium twice, and resuspended in minimal medium to prepare intact cells. Subsequently, for the reaction, HEPES (pH 7.0) as a buffer solution is added to the intact cells so that the concentration is 25 mM, and anthranilic acid or 4-amino benzoate as a substrate is added so that the final concentration is 5 mM. After shaking at 200 rpm at 33° C. for 6 hours, the reaction mixture was centrifuged to separate bacterial cells and supernatant. The supernatant is filtered through a 0.22-μm filter, and the filtrate is used as a sample. The produced aniline can be quantified by GC/MS or HPLC.

In the present invention, a DNA consisting of a base sequence which has 90% or more, preferably 95% or more, more preferably 98% or more homology with a base sequence comprising the above-described mutation and which encodes a polypeptide having aminobenzoate decarboxylase activity can also be used. In the present invention, the base sequence homology was calculated using GENE-TYX Ver. 8 (made by Genetyx).

The homologue of the DNA consisting of a base sequence comprising the above-described mutation can be selected from a DNA library of a different species by, for example, PCR or hybridization using a primer or a probe designed based on the base sequence, according to a conventional method, and as a result, a DNA which encodes a polypeptide having aminobenzoate decarboxylase activity can be obtained with a high probability.

Construction of Vector for Transformation

The DNA which encodes aminobenzoate decarboxylase is amplified by PCR and then cloned into a suitable vector which is replicable in a host.

The plasmid vector may be any plasmid vector as long as it comprises a gene responsible for autonomously replicating function in a coryneform bacterium. Specific examples of the plasmid vector include pAM330 derived from *Brevibacterium lactofermentum* 2256 (JP 58-67699 A; Miwa, K. et al., Cryptic plasmids in glutamic acid-producing bacteria. Agric. Biol. Chem. 48:2901-2903 (1984); and Yamaguchi, R. et al., Determination of the complete nucleotide sequence of the *Brevibacterium lactofermentum* plasmid pAM330 and the analysis of its genetic information. Nucleic Acids Symp. Ser. 16:265-267 (1985)); pHM1519 derived from *Corynebacterium glutamicum* ATCC13058 (Miwa, K. et al., Cryptic plasmids in glutamic acid-producing bacteria. Agric. Biol. Chem. 48:2901-2903 (1984)) and pCRY30 derived from the same (Kurusu, Y. et al., Identification of plasmid partition function in coryneform bacteria. Appl. Environ. Microbiol. 57:759-764(1991)); pCG4 derived from *Corynebacterium glutamicum* T250 (JP 57-183799 A; and Katsumata, R. et al., Protoplast transformation of glutamate-producing bacteria with plasmid DNA. J. Bacteriol., 159: 306-311 (1984)), pAG1, pAG3, pAG14 and pAG50 derived from the same (JP 62-166890 A), and pEK0, pEC5 and pEKEx1 derived from the same (Eikmanns, B. J. et al., A family of *Corynebacterium glutamicum*/*Escherichia coli* shuttle vectors for cloning, controlled gene expression, and promoter probing. Gene, 102:93-98(1991)); etc.

Examples of a preferred promoter include promoter PgapA as a promoter of the glyceraldehyde-3-phosphate dehydrogenase A gene (gapA), promoter Pmdh as a promoter of the malate dehydrogenase gene (mdh), and promoter PldhA as a promoter of lactate dehydrogenase A gene (ldhA), all of which are derived from *Corynebacterium glutamicum* R, and inter alia, PgapA is preferred.

Examples of a preferred terminator include terminator rrnB T1T2 of *Escherichia coli* rRNA operon, terminator trpA of *Escherichia coli*, and terminator trp of *Brevibacterium lactofermentum*, and inter alia, terminator rrnB T1T2 is preferred.

Transformation

As a method of transformation, any publicly known method can be used without limitation. Examples of such a known method include the calcium chloride/rubidium chloride method, the calcium phosphate method, DEAE-dextran transfection, and electroporation. Inter alia, preferred for a coryneform bacterium is electroporation, which can be performed by a known method (Kurusu, Y. et al., Electroporation-transformation system for Coryneform bacteria by auxotrophic complementation, Agric. Biol. Chem. 54:443-447 (1990); and Vertes A. A. et al., Presence of mrr- and mcr-like restriction systems in Coryneform bacteria. Res. Microbiol. 144:181-185 (1993)).

The transformant is cultured using a culture medium usually used for culture of microorganisms. The culture medium may be a natural or synthetic medium containing a carbon source, a nitrogen source, inorganic salts, other nutritional substances, etc.

Examples of the carbon source used for the transformant include carbohydrates and sugar alcohols such as glucose, fructose, sucrose, mannose, maltose, mannitol, xylose, arabinose, galactose, starch, molasses, sorbitol and glycerol; organic acids such as acetic acid, citric acid, lactic acid, fumaric acid, maleic acid and gluconic acid; and alcohols such as ethanol and propanol. Hydrocarbons, such as normal paraffin, etc. may also be used as desired. These carbon sources may be used alone or as a mixture of two or more thereof. The concentration of these carbon sources in the culture medium is usually about 0.1 to 10 w/v %.

Examples of the nitrogen source used for the transformant include inorganic or organic ammonium compounds, such as ammonium chloride, ammonium sulfate, ammonium nitrate, and ammonium acetate; urea; aqueous ammonia; sodium nitrate; and potassium nitrate. Nitrogen-containing organic compounds, such as corn steep liquor, meat extract, peptone, N—Z-amine, protein hydrolysate, amino acid, etc. may also be used. These nitrogen sources may be used alone or as a mixture of two or more thereof. The concentration of these nitrogen sources in the culture medium varies depending on the kind of the nitrogen compound, but is usually about 0.1 to 10 w/v %.

Examples of the inorganic salts used for the transformant include potassium dihydrogen phosphate, dipotassium hydrogenphosphate, magnesium sulfate, sodium chloride, iron(II) nitrate, manganese sulfate, zinc sulfate, cobalt sulfate, and calcium carbonate. These inorganic salts may be used alone or as a mixture of two or more thereof. The concentration of the inorganic salts in the culture medium varies depending on the kind of the inorganic salts, but is usually about 0.01 to 1 w/v %.

Examples of the nutritional substances used for the transformant include meat extract, peptone, polypeptone, yeast extract, dry yeast, corn steep liquor, skim milk powder, defatted soybean hydrochloric acid hydrolysate, and extract from animals, plants or microorganisms, and degradation products thereof. The concentration of the nutritional substances in the culture medium varies depending on the kind of the nutritional substances, but is usually about 0.1 to 10 w/v %. Further, vitamins may be added as needed. Examples of the vitamins include biotin, thiamine (vitamin B1), pyridoxine (vitamin B6), pantothenic acid, inositol, nicotinic acid, etc. The pH of the culture medium is preferably about 5 to 8.

Examples of the preferable microbial culture medium used for the transformant include A medium (Inui, M. et al., Metabolic analysis of *Corynebacterium glutamicum* during lactate and succinate productions under oxygen deprivation conditions. J. Mol. Microbiol. Biotechnol. 7:182-196 (2004)), BT medium (Omumasaba, C. A. et al., *Corynebacterium glutamicum* glyceraldehyde-3-phosphate dehydrogenase isoforms with opposite, ATP-dependent regulation. J. Mol. Microbiol. Biotechnol. 8:91-103 (2004)), etc.

The culture temperature is about 15 to 45° C., and the culture period is about 1 to 7 days.

Process for Producing Aniline

Aniline can be produced by a process comprising a step of allowing the above-described transformant of the present invention to react in a reaction mixture containing aminobenzoic acid, an ester thereof, and/or a salt thereof, and a step of recovering aniline from the reaction mixture.

Growth of Microorganism

Before the reaction for aniline production, the transformant is preferably cultured and grown under aerobic conditions at about 25 to 35° C. for about 12 to 48 hours.

Culture Medium

The culture medium used for aerobic culture of the transformant before the reaction may be a natural or synthetic medium containing a carbon source, a nitrogen source, inorganic salts, other nutritional substances, etc.

Examples of the carbon source that can be used in the aerobic culture include sugars (monosaccharides such as glucose, fructose, mannose, xylose, arabinose, and galactose; disaccharides such as sucrose, maltose, lactose, cellobiose, xylobiose, and trehalose; polysaccharides such as starch; and molasses); sugar alcohols such as mannitol, sorbitol, xylitol, and glycerol; organic acids such as acetic acid, citric acid, lactic acid, fumaric acid, maleic acid and gluconic acid; alcohols such as ethanol and propanol; and hydrocarbons such as normal paraffin.

These carbon sources may be used alone or as a mixture of two or more thereof.

The concentration of these carbon sources in the culture medium is usually about 0.1 to 10 w/v %.

Examples of the nitrogen source that can be used in the aerobic culture include inorganic or organic ammonium compounds, such as ammonium chloride, ammonium sulfate, ammonium nitrate, and ammonium acetate; urea; aqueous ammonia; sodium nitrate; and potassium nitrate. Nitrogen-containing organic compounds, such as corn steep liquor, meat extract, peptone, N—Z-amine, protein hydrolysate, amino acid, etc. may also be used. These nitrogen sources may be used alone or as a mixture of two or more thereof. The concentration of these nitrogen sources in the culture medium varies depending on the kind of the nitrogen compound, but is usually about 0.1 to 10 w/v %.

Examples of the inorganic salts in the aerobic culture include potassium dihydrogen phosphate, dipotassium hydrogenphosphate, magnesium sulfate, sodium chloride, iron(II) nitrate, manganese sulfate, zinc sulfate, cobalt sulfate, and calcium carbonate. These inorganic salts may be used alone or as a mixture of two or more thereof. The concentration of the inorganic salts in the culture medium varies depending on the kind of the inorganic salts, but is usually about 0.01 to 1 w/v %.

Examples of the nutritional substances in the aerobic culture include meat extract, peptone, polypeptone, yeast extract, dry yeast, corn steep liquor, skim milk powder, defatted soybean hydrochloric acid hydrolysate, and extract from animals, plants or microorganisms, and degradation products thereof. The concentration of the nutritional substances in the culture medium varies depending on the kind of the nutritional substances, but is usually about 0.1 to 10 w/v %.

Further, vitamins may be added as needed. Examples of the vitamins include biotin, thiamine (vitamin B1), pyridoxine (vitamin B6), pantothenic acid, inositol, nicotinic acid, etc. The pH of the culture medium is preferably about 6 to 8.

Specific examples of the preferable culture medium for coryneform bacteria in the aerobic culture include A medium (Inui, M. et al., Metabolic analysis of *Corynebacterium glutamicum* during lactate and succinate productions under oxygen deprivation conditions. J. Mol. Microbiol. Biotechnol. 7:182-196 (2004)), BT medium (Omumasaba, C. A. et al., *Corynebacterium glutamicum* glyceraldehyde-3-phosphate dehydrogenase isoforms with opposite, ATP-dependent regulation. J. Mol. Microbiol. Biotechnol. 8:91-103 (2004)), etc. Such a culture medium can be used after prepared so as to contain a sugar at a concentration in the above-mentioned range.

Reaction Mixture

As the reaction mixture in the aniline production of the present invention, water, a buffer solution, an inorganic salt medium, or the like, containing an aniline precursor (raw material for aniline) can be used.

As the precursor, aminobenzoic acid, an ester thereof, and/or a salt thereof may be used. As the aminobenzoic acid, 2-aminobenzoic acid (o-aminobenzoic acid; anthranilic acid), 3-aminobenzoic acid (m-aminobenzoic acid), and 4-aminobenzoic acid (p-aminobenzoic acid) are all usable. Inter alia, preferred are 2-aminobenzoic acid and 4-aminobenzoic acid because they are soluble in water and thus easy to use for the reaction.

Examples of the salt of aminobenzoic acid include a sodium salt, a potassium salt, and a hydrochloride. Examples of the ester of aminobenzoic acid include esters with alcohols having 1 to 4 carbon atoms. As the aniline precursor, salts are preferred because they are highly soluble in the reaction mixture. These precursors may be used alone or a mixture of two or more kinds.

The concentration of aminobenzoic acid, the ester thereof, and/or the salt thereof in the reaction mixture is preferably 0.1 to 500 mM, more preferably 0.5 to 300 mM, and still more preferably 1 to 200 mM. When the concentration is in the above range, aniline can be efficiently produced.

Examples of the buffer solution in the reaction mixture include a phosphate buffer, a Tris buffer, a carbonate buffer, etc. The concentration of the buffer solution is preferably about 10 to 150 mM.

Examples of the inorganic salt medium in the reaction mixture include a medium containing one or more kinds of inorganic salts including potassium dihydrogen phosphate, dipotassium hydrogenphosphate, magnesium sulfate, sodium chloride, iron(II) nitrate, manganese sulfate, zinc sulfate, cobalt sulfate, and calcium carbonate. Inter alia, preferred is a medium containing magnesium sulfate. Specific example of the inorganic salt medium include BT medium (Omumasaba, C. A. et al., *Corynebacterium glutamicum* glyceraldehyde-3-phosphate dehydrogenase isoforms with opposite, ATP-dependent regulation. J. Mol. Microbiol. Biotechnol. 8:91-103 (2004)) etc. The concentration of the inorganic salts in the medium varies depending on the kind of the inorganic salts, but is usually about 0.01 to 1 w/v %.

The pH of the reaction mixture is preferably about 5 to 8. During the reaction, the pH of the reaction mixture is preferably kept nearly neutral, in particular at around 6 to 7 using aqueous ammonia, aqueous sodium hydroxide, or the like, under the control of a pH controller (for example, Type: DT-1023 made by Able).

Reaction Conditions

The reaction temperature, that is, the temperature for keeping the transformant alive during the reaction is preferably about 20 to 40° C., and more preferably about 25 to 35° C. When the temperature is in the above range, aniline can be efficiently produced. The reaction period is preferably about 1 to 7 days, and more preferably about 1 to 3 days. The culture may be a batch process, a fed-batch process, or a continuous process. Inter alia, a batch process is preferred.

<Reducing Conditions>

The reaction may be performed under aerobic conditions or reducing conditions, but preferably is performed under reducing conditions. Under reducing conditions, coryneform bacteria do not substantially grow and can further efficiently produce aniline.

The "reducing conditions" is defined based on the oxidation-reduction potential of the reaction mixture. The oxidation-reduction potential of the reaction mixture is preferably about −200 mV to −500 mV, and more preferably about −250 mV to −500 mV. The reducing conditions of the reaction mixture can be simply estimated using resazurin indicator (in reducing conditions, decolorization from blue to colorless is observed). However, for precise measurement, a redox-potential meter (for example, ORP Electrodes made by BROADLEY JAMES) is used.

As a method of preparing a reaction mixture under reducing conditions, any publicly known method can be used without limitation. For example, as a liquid medium for preparation of the reaction mixture, an aqueous solution for a reaction mixture may be used instead of distilled water or the like. As reference for preparation of the aqueous solution for a reaction mixture, for example, the method for preparing a culture medium for strictly anaerobic microorganisms, such as sulfate-reducing microorganisms (Pfennig, N. et al.: The dissimilatory sulfate-reducing bacteria, In The Prokaryotes, A Handbook on Habitats, Isolation and Identification of Bacteria, Ed. by Starr, M. P. et al. Berlin, Springer Verlag, 926-940, 1981, or *Nogeikagaku Jikkensho*, Ed. by Kyoto Daigaku Nogakubu Nogeikagaku Kyoshitsu, Vol. 3, Sangyo Tosho, 1990, Issue 26) may be used, and such a method provides an aqueous solution under desired reducing conditions.

Specifically, by treating distilled water or the like with heat or under reduced pressure for removal of dissolved gases, an aqueous solution for a reaction mixture under reducing conditions can be obtained. In this case, for removal of dissolved gases, especially dissolved oxygen, distilled water or the like may be treated under reduced pressure of about 10 mmHg or less, preferably about 5 mmHg or less, more preferably about 3 mmHg or less, for about 1 to 60 minutes, preferably for about 5 to 40 minutes.

Alternatively, by adding a suitable reducing agent (for example, thioglycolic acid, ascorbic acid, cysteine hydrochloride, mercaptoacetic acid, thiol acetic acid, glutathione, sodium sulfide, etc.), an aqueous solution for a reaction mixture under reducing conditions can be prepared.

These methods may be suitably combined to prepare an effective aqueous solution for a reaction mixture under reducing conditions.

It is preferred to maintain the reducing conditions of the reaction mixture during the reaction. For maintenance of reducing conditions, it is preferred that oxygen from the outside of the reaction system is prevented to the utmost extent from entering the system. Specific examples of the method employed for this purpose include a method comprising encapsulating the reaction system with inert gas, such as nitrogen gas, carbon dioxide gas, etc. In some cases, for allowing the metabolic functions in the cells of the aerobic bacterium of the present invention to work effectively during the reaction, addition of a solution of various nutrients or a reagent solution for adjusting and maintaining the pH of the reaction system may be needed. In such a case, for more effective prevention of oxygen incorporation, it is effective to remove oxygen in the solutions to be added, in advance.

Recovery of Aniline

Through the culture performed in the above manner, aniline is produced in the reaction mixture. Aniline can be recovered by collecting the reaction mixture, and it is also feasible to isolate aniline from the reaction mixture by a known method. Examples of such a known method include distillation, the membrane permeation method, and the organic solvent extraction method. The distillation, the membrane permeation method, and the organic solvent extraction method have already been fully established, and therefore may be used in the present invention.

The present invention encompasses aspects in which various constitutions described above are combined within the technical scope of the present invention in such a manner that the effects of the present invention are exerted.

EXAMPLES

Hereinafter, the present invention will be described in more detail by way of Examples, but the present invention is not limited thereto. Various modifications can be made within the technical idea of the present invention by those with ordinary skill in the art.

Production Example 1

Cloning and Expression of Aniline-Producing Gene
(1) Extraction of Chromosomal DNA from Microorganism To extract chromosomal DNA from *Enterobacter cloacae* NBRC13535, the bacterium was inoculated into NBRC Medium No. 802 (10 g of polypeptone, 2 g of yeast extract, and 1 g of $MgSO_4 \cdot 7H_2O$ were dissolved in 1 L of distilled water) using a platinum loop, and cultured with shaking at 37° C. until the logarithmic growth phase. After the bacterial cells were collected, chromosomal DNA was recovered from the collected cells using a DNA extraction kit (trade name: GenomicPrep Cells and Tissue DNA Isolation Kit, made by Amersham) according to the instruction manual.
(2) Construction of Cloning Vectors
Construction of Cloning Vector pCRB22

A DNA fragment comprising a DNA replication origin sequence of pCASE1, a plasmid derived from *Corynebacterium casei* JCM12072 (hereinafter abbreviated as pCASE1-ori) and a DNA fragment comprising a cloning vector pHSG298 (made by Takara Bio, Inc.) were amplified by the following PCR method.

In the PCR, the following sets of primers were synthesized based on SEQ ID NO: 3 (pCASE1-ori sequence) and SEQ ID NO: 4 (cloning vector pHSG298) for cloning of the pCASE1-ori sequence and the cloning vector pHSG298, and were used.

Primers for pCASE1-Ori Sequence Amplification

```
(a-1);
                                        (SEQ ID NO: 5)
5'-AT AGATCT AGAACGTCCGTAGGAGC-3'

(b-1);
                                        (SEQ ID NO: 6)
5'-AT AGATCT GACTTGGTTACGATGGAC-3'
```

Primers (a-1) and (b-1) each have a BglII restriction enzyme site added thereto.

Primers for Cloning Vector pHSG298 Amplification

```
(a-2):
                                        (SEQ ID NO: 7)
5'-AT AGATCT AGGTTTCCCGACTGGAAAG-3'
```

-continued (b-2):
(SEQ ID NO: 8)
5'-AT AGATCT CGTGCCAGCTGCATTAATGA-3'

Primers (a-2) and (b-2) each have a BglII restriction enzyme site added thereto.

As the template DNA, total DNA extracted from *Corynebacterium casei* JCM12072 obtained from Japan Collection of Microorganisms (JCM) and cloning vector pHSG298 (made by Takara Bio, Inc.) were used.

Actual PCR was performed using a thermal cycler, GENEAMP PCR System 9700 (made by Applied Biosystems) and TAKARA LA TAQ (made by Takara Bio, Inc.) as a reaction reagent under the conditions described below.

Reaction Mixture:

| | |
|---|---|
| TaKaRa LA Taq ™ (5 units/μL) | 0.5 μL |
| 10× LA PCR ™ Buffer II (Mg$^{2+}$ free) | 5 μL |
| 25 mM MgCl$_2$ | 5 μL |
| dNTP Mixture (2.5 mM each) | 8 μL |
| Template DNA | 5 μL (DNA content: 1 μg or less) |
| The above 2 primers*) | 0.5 μL each (final conc.: 1 μM) |
| Sterile distilled water | 25.5 μL |

The above ingredients were mixed, and 50 μL of the reaction mixture was subjected to PCR.

*) For amplification of the pCASE1-ori sequence, a combination of primers (a-1) and (b-1), and for amplification of the cloning vector pHSG298, a combination of primers (a-2) and (b-2) were used.

PCR Cycle:
Denaturation step: 94° C., 60 seconds
Annealing step: 52° C., 60 seconds
Extension step: 72° C.
pCASE1-ori sequence: 150 seconds
Cloning vector pHSG298: 180 seconds A cycle consisting of the above 3 steps was repeated 30 times.

Using 10 μL of the above-produced reaction mixture, 0.8% agarose gel electrophoresis was performed. In the case of the pCASE1-ori sequence, an about 1.4-kb DNA fragment was detected. In the case of the cloning vector pHSG298, an about 2.7-kb DNA fragment was detected.

10 μL of the about 1.4-kb DNA fragment comprising the pCASE1-ori sequence derived from *Corynebacterium casei*, and 10 μL of the about 2.7-kb DNA fragment comprising the cloning vector pHSG298, both amplified by the above PCR, were each cut using the restriction enzyme BglII and processed at 70° C. for 10 minutes for deactivation of the restriction enzyme. Both were mixed, and 1 μL of T4 DNA ligase 10× buffer solution and 1 unit of T4 DNA ligase (made by Takara Bio, Inc.) were added thereto. Sterile distilled water was added thereto so that the total volume was 10 μL, and the mixture was allowed to react at 15° C. for 3 hours for ligation. This was named Ligation Liquid A.

Using the Ligation Liquid A, *Escherichia coli* JM109 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 μg/mL of kanamycin.

A growing strain on the culture medium was subjected to liquid culture in the usual manner. Plasmid DNA was extracted from the culture and cut using the restriction enzyme BglII to confirm the inserted fragment. As a result, in addition to an about 2.7-kb DNA fragment of the cloning vector pHSG298, an about 1.4-kb DNA fragment of the pCASE-ori sequence was confirmed.

The cloning vector comprising the pCASE1-ori sequence was named pCRB22.

Construction of Cloning Vector pCRB207

A DNA fragment comprising a promoter sequence of the gapA gene encoding the glyceraldehyde-3-phosphate dehydrogenase (hereinafter abbreviated as PgapA) derived from *Corynebacterium glutamicum* R, and a DNA fragment comprising an rrnBT1T2 bidirectional terminator sequence (hereinafter abbreviated as terminator sequence) derived from a cloning vector pKK223-3 (made by Pharmacia) were amplified by the following method.

In the PCR, the following sets of primers were synthesized based on SEQ ID NO: 9 (PgapA sequence) and SEQ ID NO: 10 (terminator sequence) for cloning of the PgapA sequence and the terminator sequence, and were used.

Primers for PgapA Sequence Amplification (a-3);
(SEQ ID NO: 11)
5'-CTCT GTCGAC CCGAAGATCTGAAGATTCCTG-3'

(b-3);
(SEQ ID NO: 12)
5'-CTCT GTCGAC GGATCC CCATGG
TGTGTCTCCTCTAAAGATTGTAGG-3'

Primer (a-3) has a SalI restriction enzyme site added thereto, and primer (b-3) has SalI, BamHI, and NcoI restriction enzyme sites added thereto.

Primers for Terminator Sequence Amplification (a-4);
(SEQ ID NO: 13)
5'-CTCT GCATGC CCATGG CTGTTTTGGCGGATGAGAGA-3'

(b-4);
(SEQ ID NO: 14)
5'-CTCT GCATGC TCATGA AAGAGTTTGTAGAAACGCAAAAAGG-3'

Primer (a-4) has SphI and NcoI restriction enzyme sites added thereto, and primer (b-4) has SphI and BspHI restriction enzyme sites added thereto.

As the template DNA, the chromosomal DNA extracted from *Corynebacterium glutamicum* R (FERM P-18976 (FERM BP-18976)) and the plasmid pKK223-3 (made by Pharmacia) were used.

Actual PCR was performed using a thermal cycler, GENEAMP PCR System 9700 (made by Applied Biosystems) and TAKARA LA TAQ (made by Takara Bio, Inc.) as a reaction reagent under the conditions described below.

Reaction Mixture:

| | |
|---|---|
| TaKaRa LA Taq ™ (5 units/μL) | 0.5 μL |
| 10× LA PCR ™ Buffer II (Mg$^{2+}$ free) | 5 μL |
| 25 mM MgCl$_2$ | 5 μL |
| dNTP Mixture (2.5 mM each) | 8 μL |
| Template DNA | 5 μL (DNA content: 1 μg or less) |
| The above 2 primers*) | 0.5 μL each (final conc.: 1 μM) |
| Sterile distilled water | 25.5 μL |

The above ingredients were mixed, and 50 μL of the reaction mixture was subjected to PCR.

*) For amplification of the PgapA sequence, a combination of primers (a-3) and (b-3), and for amplification of the terminator sequence, a combination of primers (a-4) and (b-4) were used.
Primers for Dec/LR Gene Amplification (a-5);
(SEQ ID NO: 15)
5'-CTCT CATATG ACAGCATCACCTTGGG-3'

(b-5);
(SEQ ID NO: 16)
5'-CTCT CATATG TCATCTTAACGACGCTCCATTC-3'

Primers (a-5) and (b-5) each have an NdeI restriction enzyme site added thereto.
Primers for Dec/LB Gene Amplification (a-6);
(SEQ ID NO: 17)
5'-CTCT CATATG GTAAATGATCCTTATGATTTACGAAAAG-3'

(b-6);
(SEQ ID NO: 18)
5'-CTCT CATATG CTAATCTCCCTCCCAACG-3'

Primers (a-6) and (b-6) each have an NdeI restriction enzyme site added thereto.
PCR Cycle:
  Denaturation step: 94° C., 60 seconds
  Annealing step: 52° C., 60 seconds
  Extension step: 72° C.
  PgapA sequence: 45 seconds
  Terminator sequence: 30 seconds
  A cycle consisting of the above 3 steps was repeated 30 times.

Using 10 µL of the above-produced reaction mixture, 0.8% agarose gel electrophoresis was performed. In the case of the PgapA sequence, an about 0.6-kb DNA fragment was detected. In the case of the terminator sequence, an about 0.4-kb DNA fragment was detected.

10 µL of the about 0.6-kb DNA fragment comprising the PgapA sequence derived from *Corynebacterium glutamicum* R, which was amplified by the above PCR, and the about 4.1-kb cloning vector pCRB22 were each cut using the restriction enzyme SalI and processed at 70° C. for 10 minutes for deactivation of the restriction enzyme. Both were mixed, and 1 µL of T4 DNA ligase 10× buffer solution and 1 unit of T4 DNA ligase (made by Takara Bio, Inc.) were added thereto. Sterile distilled water was added thereto so that the total volume was 10 µL, and the mixture was allowed to react at 15° C. for 3 hours for ligation. This was named Ligation Liquid B.

Using the Ligation Liquid B, *Escherichia coli* JM109 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 µg/mL of kanamycin.

A growing strain on the culture medium was subjected to liquid culture in the usual manner. Plasmid DNA was extracted from the culture and cut using the restriction enzyme SalI to confirm the inserted fragment. As a result, in addition to an about 4.1-kb DNA fragment of the cloning vector pCRB22, an about 0.6-kb DNA fragment of the PgapA sequence was confirmed.

The cloning vector comprising the PgapA sequence was named pCRB206.

10 µL of the about 0.4-kb DNA fragment comprising the terminator sequence derived from the plasmid pKK223-3, which was amplified by the above PCR, was cut using the restriction enzymes NcoI and BspHI, 2 µL of the above cloning vector pCRB206 was cut using the restriction enzyme NcoI, and both were processed at 70° C. for 10 minutes for deactivation of the restriction enzymes. Both were mixed, and 1 µL of T4 DNA ligase 10× buffer solution and 1 unit of T4 DNA ligase (made by Takara Bio, Inc.) were added thereto. Sterile distilled water was added thereto so that the total volume was 10 µL, and the mixture was allowed to react at 15° C. for 3 hours for ligation. This was named Ligation Liquid C.

Using the Ligation Liquid C, *Escherichia coli* JM109 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 µg/mL of kanamycin.

A growing strain on the culture medium was subjected to liquid culture in the usual manner. Plasmid DNA was extracted from the culture and cut using the restriction enzyme to confirm the inserted fragment. As a result, in addition to an about 4.7-kb DNA fragment of the cloning vector pCRB206, an about 0.4-kb DNA fragment of the terminator sequence was confirmed.

The cloning vector comprising the rrnBT1T2 terminator sequence was named pCRB207.
Construction of Cloning Vector pCRB209

A DNA fragment comprising a promoter sequence of the gapA (glyceraldehyde 3-phosphate dehydrogenase A) gene (hereinafter abbreviated as PgapA) derived from *Corynebacterium glutamicum* R was amplified by the following method.

In the PCR, the following set of primers was synthesized based on SEQ ID NO: 19 (pCRB207) for cloning of the pCRB207 sequence, and was used.
Primers for pCRB207 Sequence Amplification (a-7);
(SEQ ID NO: 20)
5'-CTCT CATATG CTGTTTTGGCGGATGAGAG-3'

(b-7);
(SEQ ID NO: 21)
5'-CTCT CATATG GTGTCTCCTCTAAAGATTGTAGG-3'

Primers (a-7) and (b-7) each have an NdeI restriction enzyme site added thereto.

As the template DNA, the cloning vector pCRB207 comprising a gapA promoter and a rrnBT1T2 terminator sequence was used.

Actual PCR was performed using a thermal cycler, GENEAMP PCR System 9700 (made by Applied Biosystems) and TAKARA LA TAQ (made by Takara Bio Inc.) as a reaction reagent under the conditions described below.
Reaction Mixture:

| TaKaRa LA Taq ™ (5 units/µL) | 0.5 µL |
|---|---|
| 10× LA PCR ™ Buffer II (Mg²⁺ free) | 5 µL |
| 25 mM MgCl$_2$ | 5 µL |
| dNTP Mixture (2.5 mM each) | 8 µL |
| Template DNA | 5 µL (DNA content: 1 µg or less) |
| The above 2 primers*⁾ | 0.5 µL each (final conc.: 1 µM) |
| Sterile distilled water | 25.5 µL |

The above ingredients were mixed, and 50 μL of the reaction mixture was subjected to PCR.

*) For amplification of the pCRB207 sequence, a combination of primers (a-7) and (b-7) was used.

Primers for Dec/PP Gene Amplification

```
(a-8);
                                        (SEQ ID NO: 22)
5'-CTCT CATATG AACGGGCCGGAAC-3'

(b-8);
                                        (SEQ ID NO: 23)
5'-CTCT CATATG TCAATCATCCACCCCGAAG-3'
```

Primers (a-8) and (b-8) each have an NdeI restriction enzyme site added thereto.

PCR Cycle:
Denaturation step: 94° C., 60 seconds
Annealing step: 52° C., 60 seconds
Extension step: 72° C., 307 seconds A cycle consisting of the above 3 steps was repeated 30 times.

Using 10 μL of the above-produced reaction mixture, 0.8% agarose gel electrophoresis was performed, and an about 5.1-kb DNA fragment comprising the cloning vector pCRB207 was detected.

10 μL of the about 5.1-kb DNA fragment comprising the gene derived from pCRB207, which was amplified by the above PCR, was cut using the restriction enzyme NdeI and processed at 70° C. for 10 minutes for deactivation of the restriction enzyme. To this, 1 μL of T4 DNA ligase 10× buffer solution and 1 unit of T4 DNA ligase (made by Takara Bio Inc.) were added. Sterile distilled water was added thereto so that the total volume was 10 μL, and the mixture was allowed to react at 15° C. for 3 hours for ligation. This was named Ligation Liquid D.

Using the Ligation Liquid D, Escherich-ia coli JM109 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 μg/mL of kanamycin.

A growing strain on the culture medium was subjected to liquid culture in the usual manner. Plasmid DNA was extracted from the culture and cut using the restriction enzyme NdeI to confirm the inserted restriction enzyme site.

The cloning vector comprising the PgapA sequence and the rrnBT1T2 terminator sequence was named pCRB209.

(3) Cloning of Aniline-Producing Gene Derived from *Enterobacter cloacae*

A DNA fragment comprising the ECL_04083-ECL_04082-ECL_04081 (hereinafter indicated as dec/ECL) gene which encodes aminobenzoate decarboxylase derived from *Enterobacter cloacae* was amplified by the PCR method as described below.

In the PCR, the following set of primers was synthesized based on SEQ ID NO: 24 (the dec/ECL gene of *Enterobacter cloacae*) using "394 DNA/RNA Synthesizer" made by Applied Biosystems for cloning of the dec/ECL gene, and was used.

Primers for Dec/ECL Gene Amplification

```
(a-9);
                                        (SEQ ID NO: 25)
5'-CTCT CATATG AGATTGATCGTGGGAATGAC-3'

(b-9);
                                        (SEQ ID NO: 26)
5'-CTCT CATATG TTACAGCAATGGCGGAATGG-3'
```

Primers (a-9) and (b-9) each have an NdeI restriction enzyme site added thereto.

As the template DNA for *Enterobacter cloacae*, the chromosomal DNA extracted from *Enterobacter cloacae* NBRC13535 obtained from NITE Biological Resource Center (NBRC) was used.

Actual PCR was performed using a thermal cycler, GENEAMP PCR System 9700 (made by Applied Biosystems) and TAKARA LA TAQ (made by Takara Bio, Inc.) as a reaction reagent under the conditions described below.

Reaction Mixture:

| | |
|---|---|
| TaKaRa LA Taq ™ (5 units/μL) | 0.5 μL |
| 10× LA PCR ™ Buffer II (Mg²⁺ free) | 5 μL |
| 25 mM MgCl₂ | 5 μL |
| dNTP Mixture (2.5 mM each) | 8 μL |
| Template DNA | 5 μL (DNA content: 1 μg or less) |
| The above 2 primers*⁾ | 0.5 μL each (final conc.: 1 μM) |
| Sterile distilled water | 25.5 μL |

The above ingredients were mixed, and 50 μL of the reaction mixture was subjected to PCR.

*) For amplification of the dec/ECL gene of *Enterobacter cloacae*, a combination of primers (a-9) and (b-9) was used.

PCR Cycle:
Denaturation step: 94° C., 60 seconds
Annealing step: 52° C., 60 seconds
Extension step: 72° C.

*Enterobacter cloacae* dec/ECL gene 135 seconds

A cycle consisting of the above 3 steps was repeated 30 times.

Using 10 μL of the reaction mixture produced above, 0.8% agarose gel electrophoresis was performed. As a result, detected was an about 2.3-kb DNA fragment of the *Enterobacter cloacae* dec/ECL gene.

(4) Construction of Aniline-Producing Gene Expression Plasmid Cloning of Aniline-Producing Gene to pCRB209

10 μL of the about 2.3-kb DNA fragment comprising the dec/ECL gene derived from *Enterobacter cloacae*, which was amplified by the PCR in the above (3), and 2 μL of the cloning vector pCRB209 comprising a promoter PgapA were each cut using the restriction enzyme NdeI and processed at 70° C. for 10 minutes for deactivation of the restriction enzyme. Both were mixed, and 1 μL of T4 DNA ligase 10× buffer solution and 1 unit of T4 DNA ligase (made by Takara Bio, Inc.) were added thereto. Sterile distilled water was added thereto so that the total volume was 10 μL, and the mixture was allowed to react at 15° C. for 3 hours for ligation. The resulting liquid was named Ligation Liquid E.

With the use the obtained Ligation Liquid E, *Escherichia coli* JM109 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 μg/mL of kanamycin.

A growing strain on the culture medium was subjected to liquid culture in the usual manner. Plasmid DNA was extracted from the culture and cut using the restriction enzyme to confirm the inserted fragment. As a result, in addition to an about 5.1-kb DNA fragment of the plasmid pCRB209, confirmed was an about 2.3-kb inserted fragment of the dec/ECL gene derived from *Enterobacter cloacae*.

The plasmid comprising the dec/ECL gene derived from *Enterobacter cloacae* was named pCRB209-dec/ECL (FIG. 1).

(5) Construction of Transgenic Strain for Aniline-Producing Gene

Using the above-described plasmid pCRB209-dec/ECL, transformation of *Corynebacterium glutamicum* R was performed by electroporation (Agric. Biol. Chem., Vol. 54, 443-447 (1990) and Res. Microbiol., Vol. 144, 181-185 (1993)), and the strain was applied to A agar medium (2 g of $(NH_2)_2CO_3$ 7 g of $(NH_4)_2SO_4$, 0.5 g of $KH_2PO_4$, 0.5 g of $K_2HPO_4$, 0.5 g of $MgSO_4 \cdot 7H_2O$, 1 mL of 0.06% (w/v) $Fe_2SO_4 \cdot 7H_2O + 0.042\%$ (w/v) $MnSO_4 \cdot 2H_2O$, 1 mL of 0.02% (w/v) biotin solution, 2 mL of 0.01% (w/v) thiamin solution, 2 g of yeast extract, 7 g of vitamin assay casamino acid, 40 g of glucose, and 15 g of agar were suspended in 1 L of distilled water) containing 50 μg/mL of kanamycin.

A growing strain on the culture medium was subjected to liquid culture in the usual manner. Plasmid DNA was extracted from the culture and cut using the restriction enzyme to confirm the inserted plasmid. As a result, introduction of the above-constructed plasmid pCRB209-dec/ECL was confirmed.

The strain to which the plasmid pCRB209-dec/ECL had been introduced was named *Corynebacterium glutamicum* ANI-7.

Example 1

Random mutation targeting a gene which encodes aminobenzoate decarboxylase derived from *Enterobacter cloacae* was introduced, and screening for a strain having an increased aniline productivity was performed to obtain the intended mutant strain. Specifically, the mutation was introduced using a random mutation introduction kit (trade name: GeneMorph II Random Mutagenesis Kit, made by Agilent). Specifically, using the above pCRB209-dec/ECL plasmid as a template and a combination of Primer 1 (5'-GTCGCTC-CCATATGAGATTGATCGTG-3', SEQ ID NO: 27) and Primer 2 (5'-GCTCCTGCCATATGTTACAGCAATGG-3', SEQ ID NO: 28), random mutation was introduced according to the manual attached to the kit. The DNA fragment into which the mutation had been introduced and the plasmid pCRB209 were digested using a restriction enzyme NdeI, and after the deactivation of the restriction enzyme at 70° C. for 10 minutes, purification was performed. Both were mixed, and 1 μL of T4 DNA ligase 10× buffer solution and 1 unit of T4 DNA ligase (made by Takara Bio, Inc.) were added thereto. Sterile distilled water was added thereto so that the total volume was 10 μL, and the mixture was allowed to react at 15° C. for 3 hours for ligation. This was named DNA Library Liquid F.

Using the DNA Library Liquid F, *Escherichia coli* JM109 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 μg/mL of kanamycin. A growing strain on the culture medium was subjected to liquid culture in the usual manner, and plasmid DNA was extracted from the culture medium. The DNA sequence of the plasmid of a randomly selected clone was determined to confirm the introduction of a mutation. Using the above-extracted DNA library (plasmid DNA mixture), transformation of *Corynebacterium glutamicum* R was performed by electroporation [Agric. Biol. Chem., Vol. 54, 443-447 (1990) and Res. Microbiol., Vol. 144, 181-185 (1993)], and the strain was applied to A agar medium containing 50 μg/mL of kanamycin. A growing strain on the culture medium was subjected to liquid culture in the usual manner. Plasmid DNA was extracted from the culture and cut using the restriction enzyme to confirm the inserted fragment. As a result, in addition to an about 5.1-kb DNA fragment of the plasmid pCRB209, an about 2.3-kb inserted fragment of the dec/ECL gene derived from *Enterobacter cloacae* (random mutant at P309) was confirmed.

In this mutant strain, proline (P) at position 309 from the N terminus of a 52.5 kDa subunit of three subunits (21.7 kDa, 52.5 kDa, 8.6 kDa) of aminobenzoate decarboxylase was replaced by threonine (T).

Examples 2 to 6 and Comparative Examples 2 and 3

Site-specific mutation was performed in order that proline (P) at position 309 from the N terminus in the 52.5 kDa subunit of aminobenzoate decarboxylase was replaced by an amino acid other than threonine (T). Specifically, the mutation was introduced using a random mutation introduction kit (trade name: PRIMESTAR™ Mutagenesis Basal Kit, made by Takara Bio, Inc.). Specific reaction conditions were as follows.

| | |
|---|---|
| PrimeSTARMax Premix (2×) | 25 μL |
| Primer 1 (Fwd) | 5 μL (final conc.: 0.2 μM) |
| Primer 2 (Rev) | 5 μL (final conc.: 0.2 μM) |
| Template DNA (pCRB209-dec/ECL plasmid) | 5 μL (2 pg) |
| Sterile distilled water | 10 μL |

The above ingredients were mixed, and 50 μL of the reaction mixture was subjected to PCR.

The primers used for each mutation are as follows.

Primers for Example 2 (P309R):

R (Fwd);
(SEQ ID NO: 29)
5'-GGGATGCGCTGGACCGAGATCGACTAC-3'

R (Rev);
(SEQ ID NO: 30)
5'-GGTCCAGCGCATCCCGAGATAGAGGGA-3'

Primers for Example 3 (P309S):

S (Fwd);
(SEQ ID NO: 31)
5'-GGGATGTCCTGGACCGAGATCGACTAC-3'

S (Rev);
(SEQ ID NO: 32)
5'-GGTCCAGGACATCCCGAGATAGAGGGA-3'

Primers for Example 4 (P309M):

M (Fwd);
(SEQ ID NO: 33)
5'-GGGATGATGTGGACCGAGATCGACTAC-3'

M (Rev);
(SEQ ID NO: 34)
5'-GGTCCACATCATCCCGAGATAGAGGGA-3'

Primers for Example 5 (P309V):

V (Fwd);
(SEQ ID NO: 35)
5'-GGGATGGTGTGGACCGAGATCGACTAC-3'

V (Rev);
(SEQ ID NO: 36)
5'-GGTCCACACCATCCCGAGATAGAGGGA-3'

Primers for Example 6 (P309Q):

Q (Fwd);
(SEQ ID NO: 37)
5'-GGGATGCAGTGGACCGAGATCGACTAC-3'

Q (Rev);
(SEQ ID NO: 38)
5'-GGTCCACTGCATCCCGAGATAGAGGGA-3'

Primers for Comparative Example 2 (P309A):

A (Fwd);
(SEQ ID NO: 39)
5'-GGGATGGCATGGACCGAGATCGACTAC-3'

A (Rev);
(SEQ ID NO: 40)
5'-GGTCCATGCCATCCCGAGATAGAGGGA-3'

Primers for Comparative Example 3 (P309F):

F (Fwd);
(SEQ ID NO: 41)
5'-GGGATGTTCTGGACCGAGATCGACTAC-3'

F (Rev);
(SEQ ID NO: 42)
5'-GGTCCAGAACATCCCGAGATAGAGGGA-3'

PCR Cycle:
Denaturation step: 98° C., 10 seconds
Annealing step: 98° C., 15 seconds
Extension step: 72° C., 40 seconds
A cycle consisting of the above 3 steps was repeated 30 times.

Using 5 µL of the above-produced reaction mixture, 0.8% agarose gel electrophoresis was performed, and an about 2.7-kb DNA fragment was detected.

Using the PCR reaction mixture, *Escherichia coli* JM109 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 µg/mL of kanamycin.

A growing strain on the culture medium was subjected to liquid culture in the usual manner. Plasmid DNA was extracted from the culture medium and cut using the restriction enzyme to confirm the inserted fragment. As a result, in addition to an about 5.1-kb DNA fragment of the plasmid pCRB209, an about 2.3-kb inserted fragment of the dec/ECL gene derived from *Enterobacter cloacae* (P309 mutant) was confirmed.

Also, DNA sequencing confirmed successful introduction of the intended mutation.

Construction of Transgenic Strains for Aniline-Producing Gene

Using the above-described plasmid pCRB209-dec/ECL (wild type and each of the P309 mutants), transformation of *Corynebacterium glutamicum* R was performed by elec-troporation [Agric. Biol. Chem., Vol. 54, 443-447 (1990) and Res. Microbiol., Vol. 144, 181-185 (1993)], and the strain was applied to A agar medium containing 50 µg/mL of kanamycin.

A growing strain on the culture medium was subjected to liquid culture in the usual manner. Plasmid DNA was extracted from the culture and cut using the restriction enzyme to confirm the inserted plasmid. As a result, introduction of the above-constructed plasmid pCRB209-dec/ECL was confirmed.

The strain to which the plasmid pCRB209-dec/ECL (P309A mutant) had been introduced was named *Corynebacterium glutamicum* ANI-8.

The strain to which the plasmid pCRB209-dec/ECL (P309F mutant) had been introduced was named *Corynebacterium glutamicum* ANI-9.

The strain to which the plasmid pCRB209-dec/ECL (P309T mutant) had been introduced was named *Corynebacterium glutamicum* ANI-10.

The strain to which the plasmid pCRB209-dec/ECL (P309R mutant) had been introduced was named *Corynebacterium glutamicum* ANI-11.

The strain to which the plasmid pCRB209-dec/ECL (P309S mutant) had been introduced was named *Corynebacterium glutamicum* ANI-12.

The strain to which the plasmid pCRB209-dec/ECL (P309M mutant) had been introduced was named *Corynebacterium glutamicum* ANI-13.

The strain to which the plasmid pCRB209-dec/ECL (P309V mutant) had been introduced was named *Corynebacterium glutamicum* ANI-14.

The strain to which the plasmid pCRB209-dec/ECL (P309Q mutant) had been introduced was named *Corynebacterium glutamicum* ANI-15.

*Corynebacterium glutamicum* ANI-13, ANI-14, and ANI-15 were deposited in Incorporated Administrative Agency National Institute of Technology and Evaluation (NITE) Patent Microorganisms Depositary (2-5-8 Kazusakamatari, Kisarazu-shi, Chiba 292-0818 Japan) under Accession Numbers NITE P-01583, NITE P-01584, and NITE P-01585, respectively, on Apr. 2, 2013. Also, a request for transfer of these strains to the international depositary authority based on Budapest Treaty was filed with the institute, and the transfer has already been completed (International Accession Numbers: NITE BP-01583, NITE BP-01584, and NITE BP-01585).

*Corynebacterium glutamicum* R was deposited in Incorporated Administrative Agency National Institute of Technology and Evaluation (NITE) Patent Microorganisms Depositary (2-5-8 Kazusakamatari, Kisarazu-shi, Chiba 292-0818 Japan) under Accession Number FERM P-18976 on Aug. 20, 2002. Also, a request for transfer of the strain to the international depositary authority based on Budapest Treaty was filed with the institute, and the transfer has already been completed (International Accession Number: FERM BP-18976).

The strain in which the proline at position 309 from the N terminus of the 52.5 kDa subunit of the three subunits (21.7 kDa, 52.5 kDa, 8.6 kDa) of aminobenzoate decarboxylase was replaced by alanine was used as Comparative Example 2, and the strain in which the proline at position 309 from the N terminus was replaced by phenylalanine was used as Comparative Example 3. The strain in which the proline at position 309 from the N terminus was replaced by threonine was used as Example 1. The strain in which the proline at position 309 from the N terminus was replaced by arginine was used as Example 2. The strain in which the proline at position 309 from the N terminus was replaced by serine was used as Example 3. The strain in which the praline at position 309 from the N terminus was replaced by methionine was used as Example 4. The strain in which the praline at position 309 from the N terminus was replaced by valine was used as Example 5. The strain in which the proline at position 309 from the N terminus was replaced by glutamine was used as Example 6.

Comparative Example 4

Aniline Production from 4-Aminobenzoate Using *Corynebacterium glutamicum* Transgenic Strains for Aniline-Producing Gene
(1) Aerobic Culture The *Corynebacterium glutamicum* ANI-7 strain (wild type, Comparative Example 1) constructed in Production Example 1 was applied to A agar medium (2 g of $(NH_2)_2CO_3$ 7 g of $(NH_4)_2SO_4$, 0.5 g of $KH_2PO_4$, 0.5 g of $K_2HPO_4$, 0.5 g of $MgSO_4.7H_2O$, 1 mL of 0.06% (w/v) $Fe_2SO_4.7H_2O$+ 0.042% (w/v) $MnSO_4.2H_2O$, 1 mL of 0.02% (w/v) biotin solution, 2 mL of 0.01% (w/v) thiamin solution, 2 g of yeast extract, 7 g of vitamin assay casamino acid, 40 g of glucose, and 15 g of agar were suspended in 1 L of distilled water) containing 50 µg/mL (final conc.) of kanamycin, and was left stand in the dark at 33° C. for 15 hours.

An inoculation loop of the *Corynebacterium glutamicum* ANI-7 strain grown on a plate as above was inoculated into a test tube containing 10 mL of A liquid medium (2 g of $(NH_2)_2CO_3$ 7 g of $(NH_4)_2SO_4$, 0.5 g of $KH_2PO_4$, 0.5 g of $K_2HPO_4$, 0.5 g of $MgSO_4.7H_2O$, 1 mL of 0.06 w/v % $Fe_2SO_4.7H_2O$+0.042 w/v % $MnSO_4.2H_2O$, 1 mL of 0.02 w/v % biotin solution, 2 mL of 0.01 w/v % thiamin solution, 2 g of yeast extract, 7 g of vitamin assay casamino acid, and 40 g of glucose were dissolved in 1 L of distilled water) containing 50 µg/mL of kanamycin, and aerobically cultured with shaking at 33° C. for 15 hours (preculture).

The *Corynebacterium glutamicum* ANI-7 strain grown in the above conditions was inoculated into 10 mL of A liquid medium in such a way that the initial bacterial cell concentration would be $OD_{610}$=0.1, and aerobic culture was performed with shaking at 33° C.
(2) Experiment of Aniline Production The bacterial cells cultured and grown as above were collected by centrifugation (15,000×g at 4° C. for 10 minutes). The obtained bacterial cells were suspended in 5 mL of a fresh BT liquid medium (2 g of $(NH_2)_2CO_3$ 7 g of $(NH_4)_2SO_4$, 0.5 g of $KH_2PO_4$, 0.5 g of $K_2HPO_4$, 0.5 g of $MgSO_4.7H_2O$, 1 mL of 0.06% (w/v) $Fe_2SO_4.7H_2O$+0.042% (w/v) $MnSO_4.2H_2O$, 1 mL of 0.02% (w/v) biotin solution, and 2 mL of 0.01% (w/v) thiamin solution were dissolved in 1 L of distilled water) added thereto, centrifuged again (15,000×g at 4° C. for 10 minutes), and then suspended again in a fresh BT liquid medium added thereto. MES buffer (pH 6.0), a substrate (4-aminobenzoic acid Na salt), and BT liquid medium were added so that the final concentrations in the reaction mixture might be as shown below, and the reaction (the composition of the reaction mixture and the reaction conditions were as shown below) was allowed to proceed in a water bath kept at 33° C. with stirring.

Reaction Mixture Composition:
  100 mM 4-aminobenzoic acid Na salt
  100 mM MES buffer (pH 6.0)
  Genetically-modified *Corynebacterium glutamicum* (coryneform bacterium) at final $OD_{610}$=25
  BT Medium The $OD_{610}$ shows cell density, and a higher $OD_{610}$ value means a higher cell density.
Reaction Conditions:
  Temperature: 33° C.
  Reaction vessel: Falcon tube (15 mL)
  Reducing Condition
  (oxidation-reduction potential; −450 mV)
  Stirring speed: 125 rpm The samples of Comparative Examples 2 and 3 were also subjected to the reaction as above.
(3) Analysis of Reaction Product At 24 hours and 48 hours after the start of the anaerobic reaction, 1 mL was taken from the reaction mixture. The reaction mixture was subjected to centrifugation for the removal of *Corynebacterium glutamicum*, and the supernatant was filtered through a 0.22-µm filter. The product of the prepared test sample was analyzed by HPLC. The results are shown in Table 1 below.

Example 7

Aniline Production from 4-Aminobenzoate Using *Corynebacterium glutamicum* Transgenic Strains for Aniline-Producing Gene Using the samples of Examples 1 to 6, aniline was produced under the same conditions as in Comparative Example 4. The results are shown in Table 1 below.

TABLE 1

| Sample | Sequence information | Transformant name | $OD_{610}$ | Amount of aniline produced in 24 hours (mM) | Amount of aniline produced in 48 hours (mM) |
|---|---|---|---|---|---|
| Comparative Example 1 | Wild type | ANI-7 | 25 | 1.6 | 2.2 |
| Comparative Example 2 | P309A | ANI-8 | 25 | 1.0 | 1.4 |
| Comparative Example 3 | P309F | ANI-9 | 25 | 0.8 | 1.2 |
| Example 1 | P309T | ANI-10 | 25 | 2.2 | 3.0 |
| Example 2 | P309R | ANI-11 | 25 | 2.7 | 3.3 |
| Example 3 | P309S | ANI-12 | 25 | 2.2 | 3.6 |
| Example 4 | P309M | ANI-13 | 25 | 3.5 | 4.9 |
| Example 5 | P309V | ANI-14 | 25 | 3.1 | 5.1 |
| Example 6 | P309Q | ANI-15 | 25 | 3.8 | 5.5 |

(In the table, P309A means that the proline at position 309 from the N terminus was replaced by alanine, P309F means that the proline at position 309 from the N terminus was replaced by phenylalanine, P309T means that the praline at position 309 from the N terminus was replaced by threonine, P309R means that the proline at position 309 from the N terminus was replaced by arginine, P309S means that the proline at position 309 from the N terminus was replaced by serine, P309M means that the proline at position 309 from the N terminus was replaced by methionine, P309V means that the proline at position 309 from the N terminus was replaced by valine, and P309Q means that the proline at position 309 from the N terminus was replaced by glutamine.)

Example 1 showed higher aniline productivity as compared with the wild type (Comparative Example 1). In the cases where the proline was replaced by alanine (Comparative Example 2) or by phenylalanine (Comparative Example 3), the aniline productivity was lower as compared with Example 1. In the cases where the proline was replaced by arginine (Example 2), serine (Example 3), methionine (Example 4), valine (Example 5), or glutamine (Example 6), the aniline productivity was higher as compared with Example 1. (Meanwhile, it was confirmed that the *Corynebacterium glutamicum* without any gene introduction (intact host) did not produce aniline at all under the same conditions. In this case, decomposition of aniline was not observed, either.)

Comparative Example 5

Aniline Production at Increased Cell Density
(1) Aerobic Culture

Using the wild type (Comparative Example 1), aerobic culture was performed in the same manner as in Comparative Example 4.

(2) Experiment of Aniline Production

The aerobically cultured and grown bacterial cells were collected by centrifugation (15,000×g at 4° C. for 10 minutes). The obtained bacterial cells were suspended in 5 mL of a fresh BT liquid medium added thereto, centrifuged again (15,000×g at 4° C. for 10 minutes), and then washed. Again, the obtained bacterial cells were suspended in a fresh BT liquid medium added thereto, centrifuged (15,000×g at 4° C. for 10 minutes) and washed again, and then suspended in a fresh BT liquid medium added thereto again.

MES buffer (pH 6.0), a substrate (4-aminobenzoic acid Na salt), and BT liquid medium were added so that the final concentrations in the reaction mixture might be as shown below, and the reaction (the composition of the reaction mixture and the reaction conditions were as shown below) was allowed to proceed in a water bath kept at 33° C. with stirring.

Reaction Mixture Composition:
  100 mM 4-aminobenzoic acid Na salt
  100 mM MES buffer (pH 6.0)
  Genetically-modified *Corynebacterium glutamicum*
  (coryneform bacterium) at final $OD_{610}$=150
  BT Medium The $OD_{610}$ shows cell density, and a higher $OD_{610}$ value means a higher cell density.

Reaction Conditions:
  Temperature: 33° C.
  Reaction vessel: Falcon tube (15 mL)
  Reducing Condition
  (oxidation-reduction potential; −450 mV)
  Stirring speed: 125 rpm (3) Analysis of Reaction Product At 48 hours after the start of the anaerobic reaction, 0.2 mL was taken from the reaction mixture. The reaction mixture was subjected to centrifugation for the removal of *Corynebacterium glutamicum*, and the supernatant was filtered through a 0.22-µm filter. The product of the prepared test sample was analyzed by HPLC. The results are shown in Table 2 below.

Example 8

Aniline Production at Increased Cell Density

Using the samples of Examples 4 to 6, aniline was produced under the same conditions as in Comparative Example 5. The results are shown in Table 2 below.

TABLE 2

| Sample | Sequence information | Transforman name | $OD_{610}$ | Amount of aniline produced in 48 hours (mM) |
|---|---|---|---|---|
| Comparative Example 1 | Wild type | ANI-7 | 150 | 18.4 |
| Example 4 | P309M | ANI-13 | 150 | 31.5 |
| Example 5 | P309V | ANI-14 | 150 | 34.2 |
| Example 6 | P309Q | ANI-15 | 150 | 28.8 |

A gene which encodes the wild type of aminobenzoate decarboxylase derived from *Enterobacter cloacae* was introduced to *Corynebacterium glutamicum* as a host. In the examination of aniline productivity at a cell density 6 times higher than in Comparative Example 4, high aniline productivity was shown.

A gene which encodes a site-specific mutant enzyme having replacement of the amino acid at position 309 from the N terminus in the 52.5 kDa subunit of aminobenzoate decarboxylase by methionine (Example 4), valine (Example 5), or glutamine (Example 6) was introduced into *Corynebacterium glutamicum* as a host, and as in Comparative Example 5, the aniline productivity was examined at a cell density 6 times higher than in Example 7. Each mutant showed even higher aniline productivity as compared with Table 1 in Example 7.

Test Example 1

Using *Escherichia coli* and *Corynebacterium glutamicum*, the influence of aniline on the growth of the strains was evaluated by the method shown below.

(1) *Escherichia coli*

A growth inhibition experiment in aerobic culture was performed to examine the influence of aniline on *Escherichia coli*.

*Escherichia coli* HST02 was applied to LB agar medium (1% polypeptone, 0.5% yeast extract, 0.5% NaCl and 1.5% agar) and was left stand in the dark at 37° C. for 15 hours.

An inoculation loop of the *Escherichia coli* HST02 grown on a plate as above was inoculated into a test tube containing 10 mL of LB liquid medium (1% polypeptone, 0.5% yeast extract, and 0.5% NaCl), and aerobic culture was performed with shaking at 37° C. for 13 hours.

Figure 2:
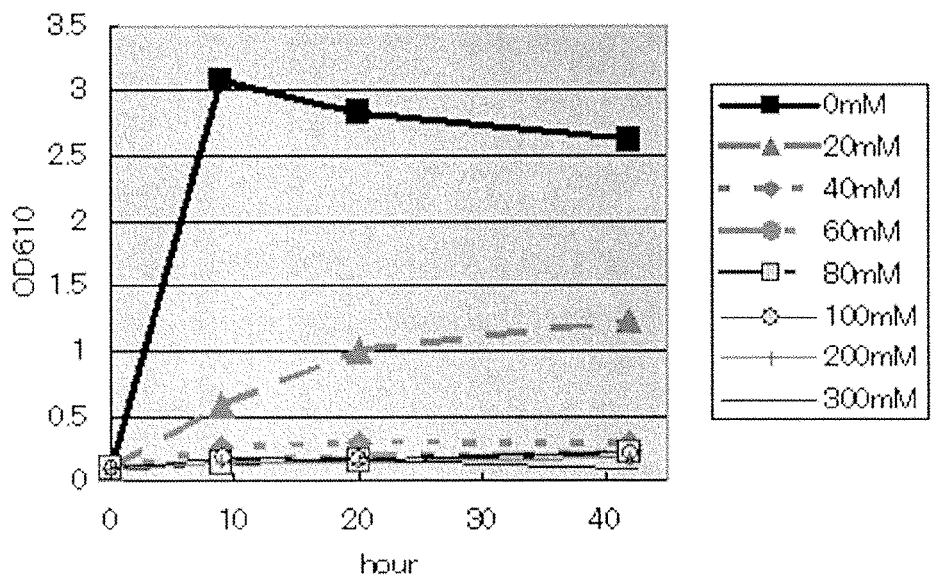
FIG. 2 shows the results of Test Example 1, where *Escherichia coli* HST02 was used for the measurement of the effect of aniline in the culture medium on the bacterial growth.

The *Escherichia coli* HST02 grown in the above conditions was inoculated into 100 mL of LB liquid medium in such a way that the initial bacterial cell concentration would be $OD_{610}$=0.1, aniline was added at the same time in such a way that the final concentration would be 0, 20, 40, 60, or 80 mM, and aerobic culture was performed with shaking at 37° C. The growth of the bacterial cells was determined by absorbance measurement at $OD_{610}$. FIG. 2 shows the analysis results of the influence of aniline addition on aerobic growth. The vertical axis of FIG. 2 indicates $OD_{610}$.

The growth of *Escherichia coli* HST02 was notably inhibited by 20 mM aniline and significantly inhibited by 40 mM aniline.

(2) *Corynebacterium glutamicum*

*Corynebacterium glutamicum* R was applied to A agar medium (2 g of $(NH_2)_2CO$, 7 g of $(NH_4)_2SO_4$, 0.5 g of $KH_2PO_4$, 0.5 g of $K_2HPO_4$, 0.5 g of $MgSO_4.7H_2O$, 1 mL of 0.06% (w/v) $Fe_2SO_4.7H_2O$+0.042% (w/v) $MnSO_4.2H_2O$, 1 mL of 0.02% (w/v) biotin solution, 2 mL of 0.01% (w/v) thiamin solution, 2 g of yeast extract, 7 g of vitamin assay casamino acid, 40 g of glucose, and 15 g of agar were suspended in 1 L of distilled water) and was left stand in the dark at 33° C. for 15 hours.

An inoculation loop of the *Corynebacterium glutamicum* R grown on a plate as above was inoculated into a test tube containing 10 mL of A liquid medium (2 g of $(NH_2)_2CO_3$ 7 g of $(NH_4)_2SO_4$, 0.5 g of $KH_2PO_4$, 0.5 g of $K_2HPO_4$, 0.5 g of $MgSO_4.7H_2O$, 1 mL of 0.06% (w/v) $Fe_2SO_4.7H_2O$+ 0.042% (w/v) $MnSO_4.2H_2O$, 1 mL of 0.02% (w/v) biotin solution, 2 mL of 0.01% (w/v) thiamin solution, 2 g of yeast extract, 7 g of vitamin assay casamino acid, and 40 g of glucose were suspended in 1 L of distilled water) and was aerobically cultured with shaking at 33° C. for 15 hours.

The *Corynebacterium glutamicum* R grown in the above conditions was inoculated into 10 mL of A liquid medium in such a way that the initial bacterial cell concentration would be $OD_{610}$=0.1, aniline was added at the same time in such a way that the final concentration would be 0, 20, 40, 60, or 80 mM, and aerobic culture was performed with shaking at 33° C. The growth of the bacterial cells was determined by absorbance measurement at $OD_{610}$.

Figure 3:
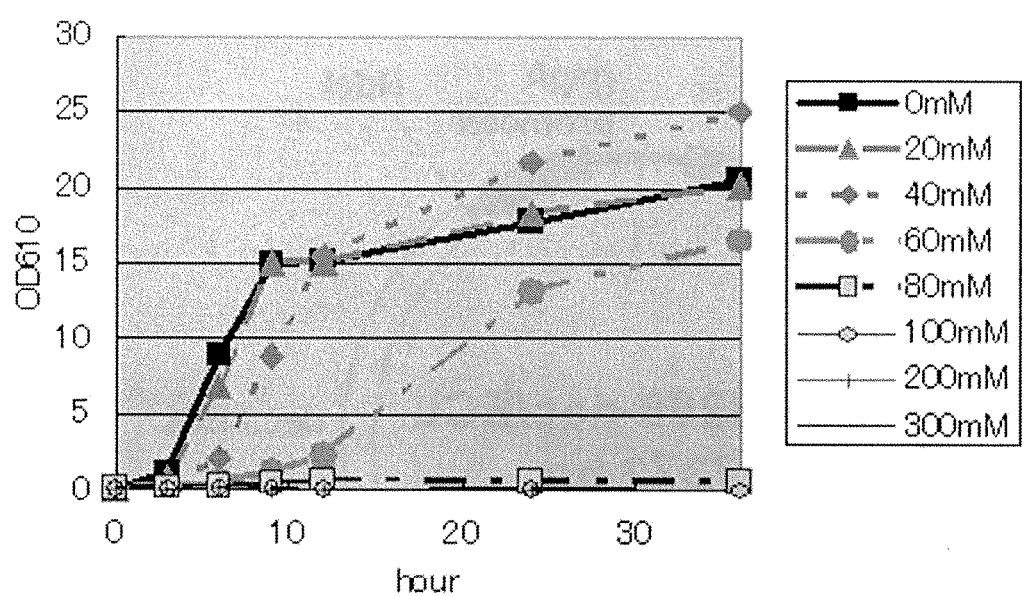
FIG. 3 shows the results of Test Example 1, where *Corynebacterium glutamicum* R was used for the measurement of the effect of aniline in the culture medium on the bacterial growth.

FIG. 3 shows the analysis results of the influence of aniline addition on aerobic growth. The vertical axis of FIG. 3 indicates $OD_{610}$.

The growth of *Corynebacterium glutamicum* was hardly affected by 40 mM aniline, which significantly affected the growth of *Escherichia coli* HST02. Even in the presence of 60 mM aniline, which completely inhibited the growth of *Escherichia coli* HST02, *Corynebacterium glutamicum* was able to grow.

Thus, it was shown that *Corynebacterium glutamicum* has a higher resistance to aniline as compared with *Escherichia coli*, and is highly suitable as a host in aniline production.

As shown above, the transformant of the present invention having an introduced mutation of proline at position 309 from the N terminus of the 52.5 kDa subunit of the three subunits (21.7 kDa subunit consisting of the amino acid sequence represented by SEQ ID NO: 43, 52.5 kDa subunit consisting of the amino acid sequence represented by SEQ ID NO: 2, and 8.6 kDa subunit consisting of the amino acid sequence represented by SEQ ID NO: 44) of an enzyme having an aminobenzoate decarboxylase activity has an excellent aniline productivity.

INDUSTRIAL APPLICABILITY

According to the process of the present invention, aniline can be produced from aminobenzoic acid with a practical efficiency using microorganisms.

The invention claimed is:

1. A *Corynebacterium* transformant that produces aniline from 4-aminobenzoic acid, wherein the transformant is transformed with a polynucleotide encoding an enzyme having aminobenzoate decarboxylase activity, wherein the amino acid sequence of the enzyme is a variant of the amino acid sequence of SEQ ID NO: 2, wherein no more than 8 amino acid residues of the amino acid sequence of the enzyme are mutated as compared to the amino acid sequence of SEQ ID NO: 2 and wherein proline (P) at the amino acid residue corresponding to position 309 of SEQ ID NO: 2 is replaced with methionine (M), valine (V), glutamine (Q), threonine (T), serine (S), or arginine (R) in the amino acid sequence of the enzyme.

2. The transformant of claim 1, wherein proline (P) at the amino acid residue corresponding to position 309 of SEQ ID NO: 2 is replaced with methionine (M), valine (V), or glutamine (Q) in the amino acid sequence of the enzyme.

3. The transformant of claim 1, wherein the polynucleotide is a variant of an *Enterobacter cloacae* aminobenzoate decarboxylase gene.

4. The transformant of claim 1, wherein the *Corynebacterium* is *Corynebacterium glutamicum*.

5. The transformant of claim 4, wherein the *Corynebacterium* is *Corynebacterium glutamicum* R having Accession No. FERM BP-18976, ATCC13032, or ATCC13869.

6. A *Corynebacterium glutamicum* transformant selected from the group consisting of the *Corynebacterium glutamicum* having National Institute of Technology and Evaluation (MITE) Accession Number BP-01583, the *Corynebacterium glutamicum* having NITE Accession Number BE-01584, and the *Corynebacterium glutamicum* having NITE Accession Number BP-01585.

7. A process for producing aniline, which comprises:
a step of allowing the transformant of claim 1 to react in a reaction mixture containing aminobenzoic acid, an ester thereof, and/or a salt thereof under reducing conditions to produce aniline, and
a step of recovering aniline from the reaction mixture.

8. The process of claim 7, wherein the transformant does not substantially grow in the reaction step.

9. The process of claim 7, wherein the oxidation-reduction potential of the reaction mixture under reducing conditions is −200 mV to −500 mV.

10. A process for producing aniline, which comprises:
a step of allowing the transformant of claim 2 to react in a reaction mixture containing aminobenzoic acid, an ester thereof, and/or a salt thereof under reducing conditions to produce aniline, and
a step of recovering aniline from the reaction mixture.

11. A process for producing aniline, which comprises:
a step of allowing the transformant of claim 3 to react in a reaction mixture containing aminobenzoic acid, an ester thereof, and/or a salt thereof under reducing conditions to produce aniline, and
a step of recovering aniline from the reaction mixture.

12. A process for producing aniline, which comprises:
a step of allowing the transformant of claim 4 to react in a reaction mixture containing aminobenzoic acid, an ester thereof, and/or a salt thereof under reducing conditions to produce aniline, and
a step of recovering aniline from the reaction mixture.

13. A process for producing aniline, which comprises:
a step of allowing the transformant of claim 5 to react in a reaction mixture containing aminobenzoic acid, an ester thereof, and/or a salt thereof under reducing conditions to produce aniline, and
a step of recovering aniline from the reaction mixture.

14. A process for producing aniline, which comprises:
a step of allowing the transformant of claim 6 to react in a reaction mixture containing aminobenzoic acid, an ester thereof, and/or a salt thereof under reducing conditions to produce aniline, and
a step of recovering aniline from the reaction mixture.

15. The process of claim 8, wherein the oxidation-reduction potential of the reaction mixture under reducing conditions is −200 mV to −500 mV.

* * * * *